(12) United States Patent
Dugovic et al.

(10) Patent No.: US 12,319,667 B2
(45) Date of Patent: Jun. 3, 2025

(54) TRICYCLO-DNA NUCLEOSIDE PRECURSORS AND PROCESSES FOR PREPARING THE SAME

(71) Applicant: Synthena AG, Bern (CH)

(72) Inventors: Branislav Dugovic, Bern (CH); Reto Bertolini, Liebefeld (CH)

(73) Assignee: Synthena AG, Bern (CH)

( * ) Notice: Subject to any disclaimer, the term of this patent is extended or adjusted under 35 U.S.C. 154(b) by 1178 days.

(21) Appl. No.: 16/960,347

(22) PCT Filed: Jan. 17, 2019

(86) PCT No.: PCT/IB2019/050401
§ 371 (c)(1),
(2) Date: Jul. 7, 2020

(87) PCT Pub. No.: WO2019/142135
PCT Pub. Date: Jul. 25, 2019

(65) Prior Publication Data
US 2020/0369639 A1    Nov. 26, 2020

Related U.S. Application Data

(60) Provisional application No. 62/619,297, filed on Jan. 19, 2018.

(51) Int. Cl.
*C07H 19/04*  (2006.01)
*C07D 307/93*  (2006.01)
(Continued)

(52) U.S. Cl.
CPC ....... *C07D 307/935* (2013.01); *C07D 307/93* (2013.01); *C07H 19/04* (2013.01); *C07H 21/04* (2013.01)

(58) Field of Classification Search
CPC ........ C12N 2310/351; C12N 2310/141; C12N 2310/323; C07H 21/00; C07H 19/04
(Continued)

(56) References Cited

FOREIGN PATENT DOCUMENTS

| EP | 2639238 A1 | 9/2013 |
|---|---|---|
| JP | 2015-513561 A | 5/2015 |

(Continued)

OTHER PUBLICATIONS

Office Action issued in corresponding Japanese Application No. 2020-539237, dated Jan. 26, 2023, 8 pages, with English translation.
(Continued)

*Primary Examiner* — Robert B Mondesi
*Assistant Examiner* — Mohammad Y Meah

(74) *Attorney, Agent, or Firm* — Morgan, Lewis & Bockius LLP

(57) ABSTRACT

The present invention relates to a process for preparing tc-DNA nucleoside precursors, the resulting tc-DNA nucleosides, and oligonucleotides comprising such tc-DNA nucleosides. In an embodiment of the invention, the process includes use of a carbene precursor. In an embodiment, the invention includes processes for preparing a tc-DNA nucleoside precursor of Formula (I), Formula (II), Formula (III), Formula (IV), Formula (V) or Formula (VI).

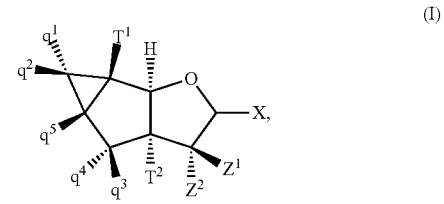

(I)

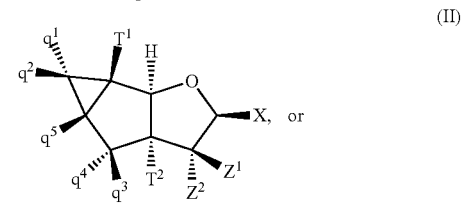

(II)

(III)

(IV)

(V)

(Continued)

-continued

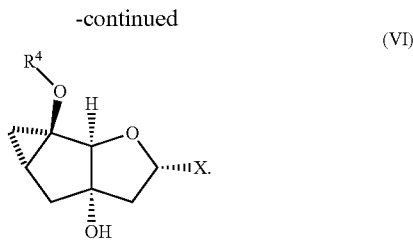

(VI)

14 Claims, 4 Drawing Sheets

(51) Int. Cl.
C07D 307/935 (2006.01)
C07H 21/04 (2006.01)
(58) Field of Classification Search
USPC .......................................................... 435/87
See application file for complete search history.

(56) References Cited

FOREIGN PATENT DOCUMENTS

JP 2016-512217 A 4/2016
WO 2014140348 A1 9/2014

OTHER PUBLICATIONS

Edwards, James P. et al., Iodomethylzinc iodide, e-EROS Encyclopedia of Reagents for Organic Synthesis, 2007, pp. 1-9.
Voituriez, Arnaud et al., Preparation of a Storable Zinc Carbenoid Species and Its Application in Cyclopropanation, Chain Extension, and [2,3]-Sigmatropic Rearrangement Reactions, Journal of Organic Chemistry, 2010, 75(4), pp. 1244-1250.
Jory Lietard et al: "Synthesis, Pairing, and Cellular Uptake Properties of C(6')-Functionalized Tricycle-DNA", Journal of Organic Chemistry, Jan. 1, 2012 (Jan. 1, 2012), pp. 4566-4577.
Ralph Steffans et al.: "Nucleic Acid Analogs with Constraint Conformational Flexibility in the Sugar-Phosphate Backbone 'Tricyclo-DNA'. Part 1. Preparation of [(5'R,6'R)-2'-deoxy-3',5'-ethano-5',6'-methano-beta-D-ribofuranosyl] thymine and -adenine, and the corresponding phosphoramidites for oligonucleotide synthesis," Helvetica Chimica Acta, vol. 80, No. 8, Dec. 15, 1997 (Dec. 15, 1997), pp. 2426-2439.
Charette AB et al: "Simmons-Smith cyclopropanation reaction", Jan. 20, 2001 (Jan. 20, 2001), Organic Reactions, John Wiley & Sons, Inc, pp. 1-415, XP002788506, ISBN: 978-0-471-10590-9 p. 7-p. 21 p. 42-p. 53.
Sibylle Frei et al: "6'-Fluoro[4.3.0]bicyclo nucleic acid: synthesis, biophysical properties and molecular dynamics simulations", Beilstein Journal of Organic Chemistry, vol. 14, Dec. 20, 2018 (Dec. 20, 2018), pp. 3088-3097.
International Search Report dated Apr. 26, 2019 for International Application No. PCT/IB2019/050401, 4 pages.
Written Opinion dated Apr. 26, 2019 for International Application No. PCT/IB2019/050401, 5 pages.
International Preliminary Report on Patenability dated Jul. 21, 2020 for International Application No. PCT/US2019/050401, 6 pages.
Final Japanese Office Action for related Japanese Patent Application No. 2020-539237, dated May 22, 2024, 4 pages.
European Office Action for related European Patent Application No. 19706745.7, dated Aug. 12, 2022, 6 pages.
European Office Action for related European Patent Application No. 19706745.7, dated Feb. 22, 2024, 4 pages.

TRICYCLO-DNA NUCLEOSIDE PRECURSORS AND PROCESSES FOR PREPARING THE SAME

STATEMENT OF RELATED APPLICATIONS

This application is a 371 U.S. National Stage application of International Patent Application No. PCT/IB2019/050401, filed Jan. 17, 2019, which claims priority to U.S. Provisional Application No. 62/619,297, filed Jan. 19, 2018, each of which is herein incorporated by reference in their entireties.

FIELD OF THE INVENTION

The invention relates to tricyclo-deoxyribonucleic acid (tc-DNA) nucleoside precursor compounds and processes for preparing such compounds as building blocks for oligomers.

BACKGROUND OF THE INVENTION

Antisense technology is an effective means for reducing the expression of specific gene products and can therefore be useful in therapeutic, diagnostic, and research applications. Generally, the principle behind antisense technology is that an antisense oligomeric compound (a sequence of nucleotides or analogues thereof) hybridizes to a target nucleic acid and modulates gene expression activities or function, such as transcription and/or translation.

Antisense oligomeric compounds may be prepared from chemically-modified antisense oligonucleotides, which may include a variety of different structural variations depending upon the therapeutic strategy. For example, tricyclo-deoxyribonucleic acids (tc-DNA) are conformationally constrained DNA analogs.

There is a need in the field for processes that allow for the bulk preparation of tc-DNA nucleoside precursors that may be used as building blocks for tc-DNA containing antisense oligonucleotide-based therapies.

SUMMARY OF THE INVENTION

In an embodiment, the invention includes processes for preparing a tc-DNA nucleoside precursor of Formula I, Formula II, Formula III, Formula IV, Formula V, or Formula VI:

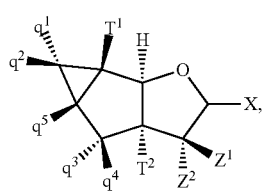
(I)

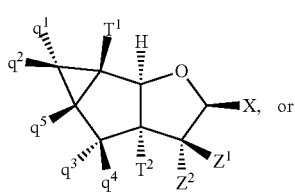
(II)

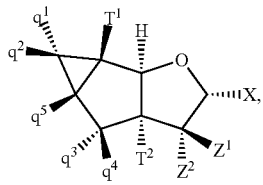
(III)

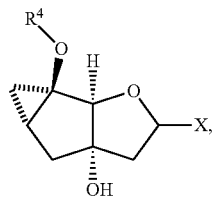
(IV)

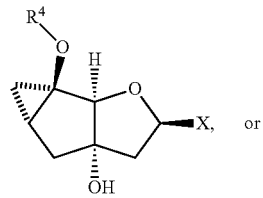
(V)

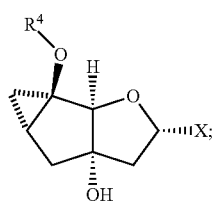
(VI)

wherein X may be alkoxy;

$T^1$ and $T^2$ may be $OR^1$, where $R^1$ is H or a hydroxyl protecting group;

$q^1$, $q^2$, $q^3$, $q^4$, and $q^5$ are each independently selected from the group consisting of hydrogen, halogen, $C_{1-6}$alkyl, $C_{2-6}$alkenyl, $C_{2-6}$alkynyl, substituted $C_{1-6}$alkyl, substituted $C_{2-6}$alkenyl, substituted $C_{2-6}$alkynyl, and $(CH_2)_n$—C(O)—$R^2$, wherein n is 0 to 6 and wherein $R^2$ is selected from the group consisting of OH, $NH_2$, O—$C_{1-32}$alkyl and NH—$C_{1-32}$alkyl; and $z^1$ and $z^2$ may each independently be selected from the group consisting of hydrogen, $C_{1-6}$alkyl, $C_{1-6}$alkoxyl, O—$C_{2-6}$alkenyl, O—$C_{2-6}$alkynyl, substituted $C_{1-6}$alkyl, substituted $C_{1-6}$alkoxy, substituted O—$C_{2-6}$alkenyl, and substituted O—$C_{2-6}$alkynyl halogen.

In an embodiment, the invention includes processes for preparing a tc-DNA nucleoside precursor of Formula VII, Formula VIII, or Formula IX:

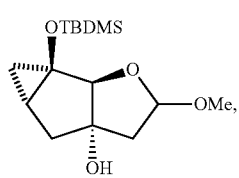
(VII)

-continued

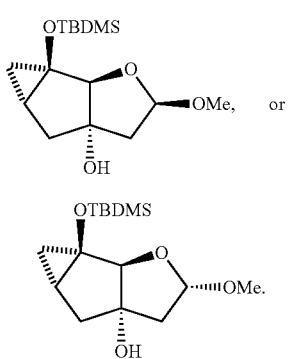
(VIII)

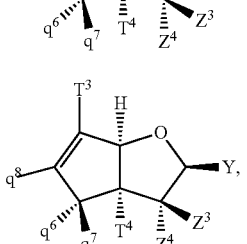
(IX)

In an embodiment, the invention includes a method of preparing a tc-DNA nucleoside precursor of any one of Formulas I-IX, the method comprising the steps of:
a. preparing a carbene precursor at a carbene preparation temperature;
b. adding a compound of Formula X, Formula XI, or Formula XII:

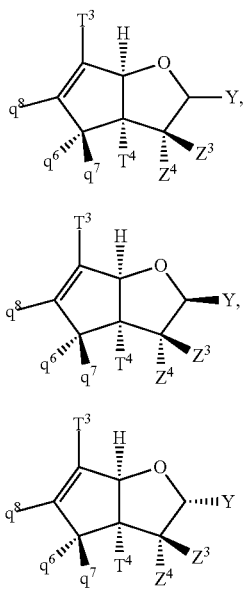

(X)

(XI)

(XII)

to the carbene precursor at a cyclopropanation temperature; and
c. providing the tc-DNA nucleoside precursor of one of Formulas I-IX,
wherein Y may be alkoxy;
$T^3$ and $T^4$ may each be $OR^5$, where $R^5$ may be H or a hydroxyl protecting group;
$q^6$, $q^7$, and $q^8$ may each be independently selected from the group consisting of hydrogen, halogen, $C_{1-6}$alkyl, $C_{2-6}$alkenyl, $C_{2-6}$alkynyl, substituted $C_{1-6}$alkyl, substituted $C_{2-6}$alkenyl, substituted $C_{2-6}$alkynyl, and $(CH_2)_n$—C(O)—$R^6$, wherein n is 0 to 6 and wherein $R^6$ is selected from the group consisting of OH, $NH_2$, O—$C_{1-32}$lkyl and NH—$C_{1-32}$alkyl; and $z^3$ and $z^4$ may each be independently selected from the group consisting of hydrogen, $C_{1-6}$alkyl, $C_{1-6}$alkoxyl, O—$C_{2-6}$alkenyl, O—$C_{2-6}$alkynyl, substituted $C_{1-6}$alkyl, substituted $C_{1-6}$alkoxy, substituted O—$C_{2-6}$alkenyl, and substituted O—$C_{2-6}$alkynyl halogen.

In an embodiment, the invention includes a method of preparing a tc-DNA nucleoside precursor of any one of Formulas I-IX, the method comprising the steps of:
a. preparing a carbene precursor at a carbene preparation temperature;
b. preparing a solution of a compound of Formula X, Formula XI, or Formula XII:

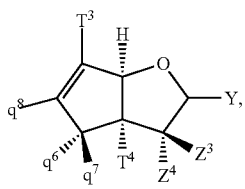
(X)

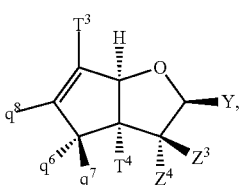
(XI)

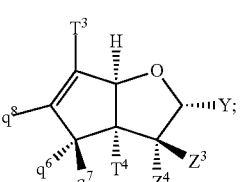
(XII)

c. adding the carbene precursor to the solution of the compound of Formula X, Formula XI, or Formula XII, at a cyclopropanation temperature; and
d. providing the tc-DNA nucleoside precursor of one of Formulas I-IX,
wherein Y may be alkoxy;
$T^3$ and $T^4$ may each be $OR^5$, where $R^5$ may be H or a hydroxyl protecting group;
$q^6$, $q^7$, and $q^8$ may each be independently selected from the group consisting of hydrogen, halogen, $C_{1-6}$alkyl, $C_{2-6}$alkenyl, $C_{2-6}$alkynyl, substituted $C_{1-6}$alkyl, substituted $C_{2-6}$alkenyl, substituted $C_{2-6}$alkynyl, and $(CH_2)_n$—C(O)—$R^6$, wherein n is 0 to 6 and wherein $R^6$ may be selected from the group consisting of OH, $NH_2$, O—$C_{1-32}$alkyl and NH—$C_{1-32}$alkyl; and $z^3$ and $z^4$ may each be independently selected from the group consisting of hydrogen, $C_{1-6}$alkyl, $C_{1-6}$alkoxyl, O—$C_{2-6}$alkenyl, O—$C_{2-6}$alkynyl, substituted $C_{1-6}$alkyl, substituted $C_{1-6}$alkoxy, substituted O—$C_{2-6}$alkenyl, and substituted O—$C_{2-6}$alkynyl halogen.

In an embodiment, the step of preparing the carbene precursor may include combining a Lewis acid catalyst (e.g., $ZnEt_2$) and $R^7I_2$ in a solvent. In some embodiments, $R^7$ may be selected from the group consisting of $CH_2$, CH—$C_{1-6}$alkyl, CH—$C_{2-6}$alkenyl, CH—$C_{2-6}$alkynyl, substituted CH—$C_{1-6}$alkyl, substituted CH—$C_{2-6}$alkenyl, substituted CH—$C_{2-6}$alkynyl, and CH—$(CH_2)_n$—C(O)—$R^8$, wherein n is 0 to 6 and wherein $R^8$ is selected from the group consisting of OH, $NH_2$, O—$C_{1-32}$alkyl and NH—$C_{1-32}$alkyl. In some embodiments, $R^7$ is alkyl. In some embodiments, $R^7$ is $CH_2$.

In some embodiments, the step of preparing the carbene precursor includes the step of adding a carbene additive to the mixture of a Lewis acid catalyst (e.g., ZnEt$_2$) and R$^7$I$_2$, wherein the carbene additive is selected from the group consisting of substituted or unsubstituted alkyl alcohol, carboxylic acid, and phosphate.

In some embodiments, the step of preparing the carbene precursor includes the step of adding a Lewis acid catalyst (e.g., ZnEt$_2$) to a mixture of a carbene additive and R$^7$I$_2$, wherein the carbene additive is selected from the group consisting of substituted or unsubstituted alkyl alcohol, carboxylic acid, and phosphate.

In some embodiments, the step of preparing the carbene precursor includes the step of adding a R$^7$I$_2$ to a mixture of a Lewis acid catalyst (e.g., ZnEt$_2$) and a carbene additive, wherein the carbene additive is selected from the group consisting of substituted or unsubstituted alkyl alcohol, carboxylic acid, and phosphate.

In some embodiments, the step of preparing the carbene precursor includes the step of adding a Lewis acid catalyst (e.g., ZnEt$_2$) and R$^7$I$_2$ to a carbene additive, wherein the carbene additive is selected from the group consisting of substituted or unsubstituted alkyl alcohol, carboxylic acid, and phosphate.

In some embodiments, the step of preparing the carbene precursor includes the step of combining a Lewis acid catalyst (e.g., ZnEt$_2$), R$^7$I$_2$ and a carbene additive, wherein the carbene additive is selected from the group consisting of substituted or unsubstituted alkyl alcohol, carboxylic acid, and phosphate.

In some embodiments, the carbene additive may be an aliphatic alcohol (e.g, substituted or unsubstituted alkyl alcohol), an aromatic alcohol (e.g., substituted or unsubstituted phenol), a substituted or unsubstituted carboxylic acid (e.g., trichloroacetic acid), or a substituted or unsubstituted phosphate (e.g., (alkyl-O)$_2$P(O)OH or (aryl-O)$_2$P(O)OH). In some embodiments, the carbene additive may be a substituted carboxylic acid of the formula Q$_3$CCO$_2$H, wherein each Q may be independently selected from the group consisting of H, Cl, Br, and F. In some embodiments, the carbene additive may be a substituted carboxylic acid of the formula Q$_3$CCO$_2$H, wherein Q$_3$C may be defined as CCl$_3$, CHCl$_2$, CH$_2$Cl, or CF$_3$. In some embodiments, the carbene additive may be a substituted alkyl alcohol of the formula Q$_3$CCH$_2$OH, wherein each Q may be independently selected from the group consisting of H, Cl, Br, and F. In some embodiments, the carbene additive may be a substituted carboxylic acid of the formula Q$_3$CCH$_2$OH, wherein Q$_3$C may be defined as CCl$_3$, CHCl$_2$, CH$_2$Cl, or CF$_3$. In some embodiments, the carbene additive may be trichloroacetic acid, 2,2,2-trifluoroethanol, thrichlorophenol, or (n-BuO)$_2$P(O)OH.

In some embodiments, the carbene precursor is Q$_3$CCO$_2$ZnR$^7$I, Q$_3$CCH$_2$OZnR$^7$I, (n-BuO)$_2$P(O)OZnR$^7$I, (alkyl-O)$_2$P(O)OZnR$^7$I, (aryl-O)$_2$P(O)OZnR$^7$I, or 2,4,6-Cl$_3$C$_6$H$_2$OZnR$^7$I, wherein each Q is independently selected from the group consisting of H, Cl, Br, and F, and R$^7$ is selected from the group consisting of CH$_2$, CH—C$_{1-6}$alkyl, CH—C$_{2-6}$alkynyl, substituted CH—C$_{1-6}$alkyl, substituted CH—C$_{2-6}$alkenyl, substituted CH—C$_{2-6}$alkynyl, and CH—(CH$_2$)—C(O)—R$^8$, wherein n is 0 to 6 and wherein R$^8$ is selected from the group consisting of OH, NH$_2$, O—C$_{1-32}$alkyl and NH—C$_{1-32}$alkyl.

In some embodiments, the carbene precursor is CCl$_3$CO$_2$ZnR$^7$I, CF$_3$CH$_2$OZnR$^7$I, (n-BuO)$_2$P(O)OZnR$^7$I, or 2,4,6-Cl$_3$C$_6$H$_2$OZnR$^7$I.

In some embodiments, the carbene precursor is CCl$_3$CO$_2$ZnCH$_2$I, CF$_3$CH$_2$OZnCH$_2$I, (n-BuO)$_2$P(O)OZnCH$_2$I, or 2,4,6-Cl$_3$C$_6$H$_2$OZnCH$_2$I.

In an embodiment, the invention includes a tc-DNA nucleoside precursor prepared according to the method described herein.

In an embodiment, the invention includes a tc-DNA nucleoside prepared from the tc-DNA nucleoside precursors described herein.

In an embodiment, the invention includes a tc-DNA containing oligonucleotide comprising a tc-DNA nucleoside described herein.

BRIEF DESCRIPTION OF THE DRAWINGS

The foregoing summary, as well as the following detailed description of the invention, will be better understood when read in conjunction with the appended drawings.

DETAILED DESCRIPTION OF THE INVENTION

Figure 1:
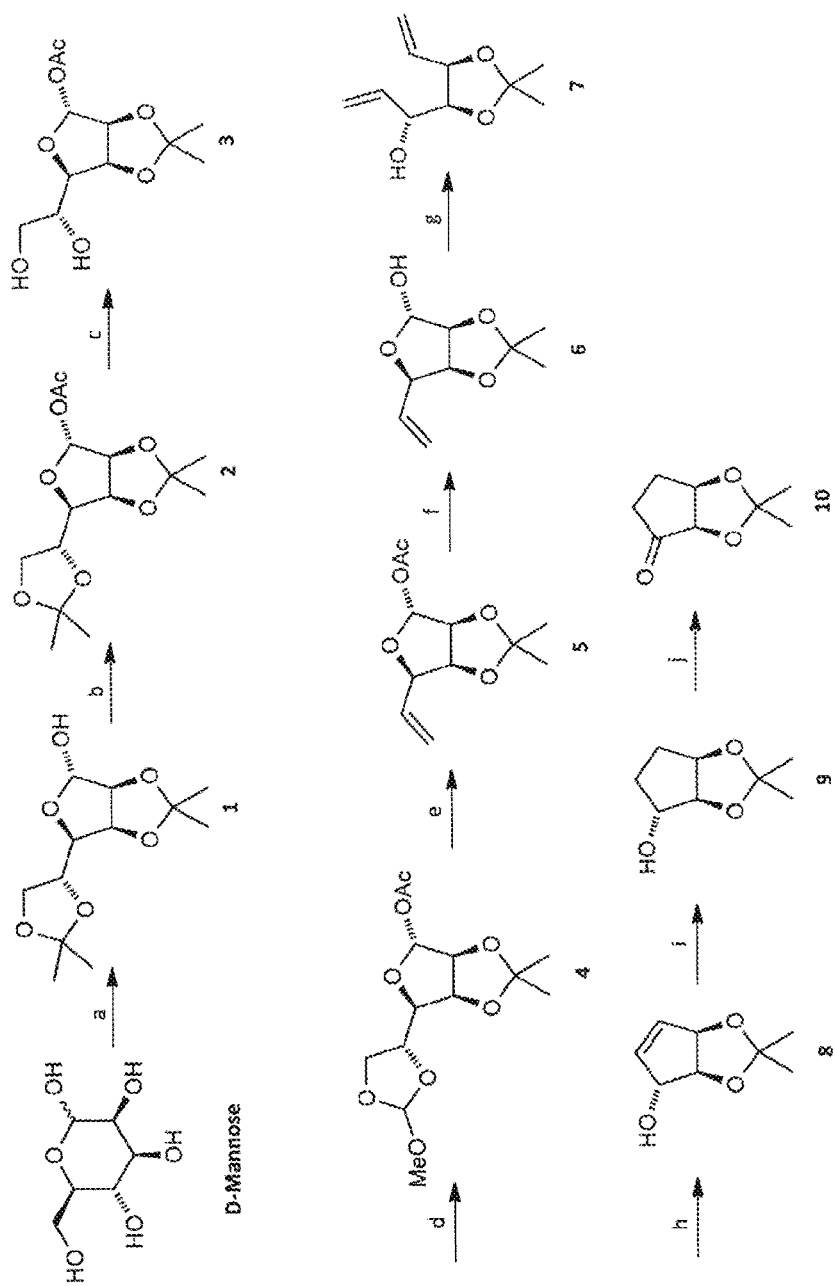
FIG. 1 illustrates a synthetic route to a bicyclo sugar intermediate 10 from D-Mannose. The reagents and conditions used in the synthetic route are as follows: (a) Me$_2$C(OMe)$_2$ (4.4 eq.), TsOH (0.003 eq.), 50° C., 1 h; (b) Ac$_2$O (2 eq.), pyridine, rt, 16 h; (c) 64% aq. AcOH, 55° C., 4 h; (d) HC(OMe)$_3$ (5 eq.), reflux, 1 h; (e) Ac$_2$O (7.4 eq.), 130° C., 3 h; (f) MeOH, t-BuOK (0.4 eq.), rt, 46% from D-Mannose; (g) NaH (1.7 eq.), DMSO (3 eq.), BrCH$_2$P(Ph)$_3$ (2 eq.), THF, 65° C., 4 h, 60% yield; (h) Grubbs I (0.005 eq.), CH$_2$Cl$_2$, rt, 16 h, 97% yield; (i) 10% Pd/C, H$_2$, MeOH, rt, 16 h, 97% yield; and (j) PCC (1.7 eq.), CH$_2$Cl$_2$, rt, 16 h, 85% yield. 20% yield from D-Mannose over 10 steps.

Unless defined otherwise, all technical and scientific terms used herein have the same meaning as is commonly understood by one of skill in the art to which this invention belongs. The headings used herein are solely for convenience reasons and should not be construed as limiting for the disclosure of any of the aspects and embodiments of the present invention. All patents and publications referred to herein are incorporated by reference in their entireties.

Definitions

The term "oligomeric compound," as used herein, refers to a compound comprising preferably eight or more monomer subunits linked by internucleosidic linkage groups, wherein at least two of said eight or more monomer subunits are tricyclo-deoxyribonucleic acid (tc-DNA) nucleosides.

The term "monomer subunit", as used herein, is meant to include all manner of monomer units that are amenable to oligomer synthesis including, and typically and preferably referring to, monomer subunits such as α-D-ribonucleosides, β-D-ribonucleosides, α-D-2'-deoxyribonucleosides, β-D-2'-deoxyribonucleosides, naturally occurring nucleosides, modified nucleosides, and hereby in particular tricyclo-deoxyribonucleic acid (tc-DNA) nucleosides and 2'-modified ribonucleic acid (2'-modified-RNA) nucleosides, locked nucleic acid (LNA) nucleosides, peptide nucleic acids (PNAs) nucleosides, 2'-deoxy T-fluoro-arabino nucleosides, hexitol nucleic acids (HNAs) nucleosides; and phosphorodiamidate morpholino (PMO) nucleosides, mimetics of nucleosides, naturally occurring nucleotides, modified nucleotides, and hereby in particular tricyclo-deoxyribonucleic acid (tc-DNA) nucleotides and 2'-modified ribonucleic acid (2'-modified-RNA) nucleotides, and mimetics of nucleotides. Typically and preferably, the term "monomer subunit", as used herein, refers to naturally occurring nucleosides and modified nucleosides, and hereby in particular to ribonucleosides, deoxyribonucleosides, tricyclo-deoxyribonucleic acid (tc-DNA) nucleosides, 2'-modified ribonucleic acid (2'-modified-RNA) nucleosides, locked nucleic acid (LNA) nucleosides, peptide nucleic acids (PNAs) nucleosides, 2'-deoxy 2'-fluoro-arabino nucleosides, hexitol nucleic acids (HNAs) nucleosides and phosphorodiamidate morpholino (PMO) nucleosides, and to naturally occurring nucleotides and modified nucleotides, and hereby in particular to ribonucleotides, deoxyribonucleotides, tricyclo-deoxyribonucleic acid (tc-DNA) nucleotides, 2'-modified ribonucleic acid (2'-modified-RNA) nucleotides, locked nucleic acid (LNA) nucleotides, peptide nucleic acids (PNAs) nucleotides, 2'-deoxy 2'-fluoro-arabino nucleotides, hexitol nucleic acids (HNAs) nucleotides and phosphorodiamidate morpholino (PMO) nucleotides. Further preferably, the term "monomer subunit," as used herein, refers to modified nucleotides, and hereby in particular tricyclo-deoxyribonucleic acid (tc-DNA) nucleotides and 2'-modified ribonucleic acid (2'-modified-RNA) nucleotides.

The term "alkylphosphate moiety" as used herein refers to groups of $C_{3-32}$alkyl-O—P(O)(OH)—O—, wherein said $C_{3-32}$alkyl is independently selected from $C_{3-32}$alkyl as defined herein.

The term "alkylphosphonate moiety" as used herein refers to groups of $C_{1-32}$alkyl-O—P(O)—O—, wherein said $C_{1-32}$alkyl is independently selected from $C_{1-32}$alkyl as defined herein.

The term "alkyl," as used herein, refers to a straight or branched hydrocarbon chain radical consisting solely of carbon and hydrogen atoms, containing no unsaturation, having from one to thirty-two carbon atoms (e.g., ($C_{1-32}$) alkyl or $C_{1-32}$ alkyl), and which may be or typically is attached to the rest of the molecule by a single bond. Whenever it appears herein, a numerical range such as "1 to 32" refers to each integer in the given range. For example, "1 to 32 carbon atoms" means that the alkyl group may consist of 1 carbon atom, 2 carbon atoms, 3 carbon atoms, etc., up to and including 32 carbon atoms, although the definition is also intended to cover the occurrence of the term "alkyl" where no numerical range is specifically designated. Typical alkyl groups include, but are not limited to, methyl, ethyl, n-propyl, 1-methylethyl (interchangeably used with iso-propyl; interchangeably abbreviated herein as iPr or Pri), n-butyl, isobutyl, sec-butyl, isobutyl, tertiary butyl (interchangeably used with 1,1-dimethylethyl or tert-butyl), n-pentyl, isopentyl, neopentyl, hexyl, septyl, octyl, nonyl and decyl. Unless stated otherwise specifically in the specification, an alkyl group is optionally substituted by one or more of substituents which are independently alkenyl, alkoxy, carboxylic group (—COOH), heteroalkyl, heteroalkenyl, hydroxyl, phosphate group (—OP(O)(OH)O—), phosphonate group (—OP(O)O—), phenyl group (—$C_6H_4$) optionally substituted with a halogen, preferably iodine, or a carboxylic group. Preferably, the term "alkyl", as used herein, refers to an unsubstituted alkyl as defined herein.

The term "alkylene," as used herein, refers to a straight or branched hydrocarbon chain bi-radical derived from alkyl, as defined herein, wherein one hydrogen of said alkyl is cleaved off generating the second radical of said alkylene. Examples of alkylene are, by way of illustration, —$CH_2$—, —$CH_2$—$CH_2$—, —$CH(CH_3)$—, —$CH_2$—$CH_2$—$CH_2$—, —$CH(CH_3)$—$CH_2$—, or —$CH(CH_2CH_3)$—.

The term "alkenyl," as used herein, refers to a straight or branched hydrocarbon chain radical group consisting solely of carbon and hydrogen atoms, containing at least one double bond, and having from 2 to 32 carbon atoms (i.e., ($C_{2-32}$)alkenyl or $C_{2-32}$alkenyl), which may be or typically is attached to the rest of the molecule by a single bond. Whenever it appears herein, a numerical range such as "2 to 32" refers to each integer in the given range—e.g., "2 to 32 carbon atoms" means that the alkenyl group may consist of 2 carbon atoms, 3 carbon atoms, 4 carbon atoms, etc., up to and including 32 carbon atoms. Typical alkenyl groups include, but are not limited to ethenyl (i.e., vinyl), prop-1-enyl (i.e., allyl), but-1-enyl, pent-1-enyl and penta-1,4-dienyl. Whenever applicable, e.g., when substituted, each double bond can be of either the (E)- or (Z)-configuration. Alkenyl, thus, may include, if applicable, either each of said double bond in its (E)-configuration, in its (Z)-configuration and mixtures thereof in any ratio. Unless stated otherwise specifically in the specification, an alkenyl group is optionally substituted by one or more of substituents which are independently alkenyl, alkoxy, carboxylic group (—COOH), heteroalkyl, heteroalkenyl, hydroxyl, phosphate group (—OP(O)(OH)O—), phosphonate group (—OP(O)O—), phenyl group (—$C_6H_4$) optionally substituted with a halogen, preferably iodine, or a carboxylic group. Preferably, the term "alkenyl", as used herein, refers to an unsubstituted alkenyl as defined herein.

The term "alkenylene", as used herein, refers to a straight or branched hydrocarbon chain bi-radical derived from alkenyl, as defined herein, wherein one hydrogen of said alkenyl is cleaved off generating the second radical of said alkenylene.

The term "alkynyl" refers to a straight or branched hydrocarbon chain radical group consisting solely of carbon and hydrogen atoms, containing at least one triple bond, having from two to ten carbon atoms (i.e., ($C_{2-32}$)alkynyl or $C_{2-32}$alkynyl). Whenever it appears herein, a numerical range such as "2 to 32" refers to each integer in the given range—e.g., "2 to 32 carbon atoms" means that the alkynyl group may consist of 2 carbon atoms, 3 carbon atoms, etc., up to and including 32 carbon atoms. Typical alkynyl groups include, but are not limited to ethynyl, propynyl, butynyl, pentynyl and hexynyl. Unless stated otherwise specifically in the specification, an alkynyl group is optionally substituted by one or more of substituents which are independently alkenyl, carboxylic group (—COOH), heteroalkyl, heteroalkenyl, phosphate group (—OP(O)(OH)O—), phosphonate group (—OP(O)O—), phenyl group (—C$_6$H$_4$) optionally substituted with a halogen, preferably iodine, or a carboxylic group. Preferably, the term "alkynyl", as used herein, refers to an unsubstituted alkynyl as defined herein.

The term "alkynylene", as used herein, refers to a straight or branched hydrocarbon chain bi-radical derived from alkynyl, as defined herein, wherein one hydrogen of said alkynyl is cleaved off generating the second radical of said alkynylene.

The term "alkoxy" refers to the group —O-alkyl, including from 1 to 32 carbon atoms of a straight, branched configuration and combinations thereof attached to the parent structure through an oxygen. Examples include, but are not limited to, methoxy, ethoxy, propoxy, isopropoxy, cyclopropyloxy and cyclohexyloxy. "Lower alkoxy" refers to alkoxy groups containing one to six carbons, also referred to as (C$_{1-6}$)alkoxy or O—C$_{1-6}$alkyl.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more of substituents which are independently alkenyl, carboxylic group (—COOH), heteroalkyl, heteroalkenyl, phosphate group (—OP(O)(OH)O—), phosphonate group (—OP(O)O—), phenyl group (—C$_6$H$_4$) optionally substituted with a halogen, preferably iodine, or a carboxylic group.

The term "acyl" refers to the groups (alkyl)-C(O)—, (aryl)-C(O)—, (heteroaryl)-C(O)—, and (heteroalkyl)-C(O)—, wherein the group is attached to the parent structure through the carbonyl functionality. Unless stated otherwise specifically in the specification, the alkyl, aryl or heteroaryl moiety of the acyl group is optionally substituted by one or more of substituents which are independently alkenyl, carboxylic group (—COOH), heteroalkyl, heteroalkenyl, phosphate group (—OP(O)(OH)O—), phosphonate group (—OP(O)O—), phenyl group (—C$_6$H$_4$) optionally substituted with a halogen, preferably iodine, or a carboxylic group.

The terms "amino" or "amine" refers to a —N(R$^a$)$_2$ radical group, where each R$^1$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N(R$^a$)$_2$ group has two R$^a$ substituents other than hydrogen, they can be combined with the nitrogen atom to form a 4-, 5-, 6- or 7-membered ring. For example, —N(R$^a$)$_2$ is intended to include, but is not limited to, 1-pyrrolidinyl and 4-morpholinyl. Unless stated otherwise specifically in the specification, an amino or amine group is optionally substituted by one or more of substituents which are independently alkenyl, carboxylic group (—COOH), heteroalkyl, heteroalkenyl, phosphate group (—OP(O)(OH)O—), phosphonate group (—OP(O)O—), phenyl group (—C$_6$H$_4$) optionally substituted with a halogen, preferably iodine, or a carboxylic group.

The terms "aromatic" or "aryl" or "Ar" refers to an aromatic radical with six to ten ring atoms (e.g., C$_6$-C$_{10}$ aromatic or C$_6$-C$_{10}$aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups.

The terms "aralkyl" or "arylalkyl" refers to an (aryl)alkyl-radical where aryl and alkyl are as disclosed herein and which are optionally substituted by one or more of the substituents described as suitable substituents for aryl and alkyl respectively.

The term "carboxyl" or "carboxylic", as interchangeably used herein, refers to a —(C═O)OH radical.

The term "cycloalkyl" refers to a monocyclic or polycyclic radical that contains only carbon and hydrogen, and may be saturated, or partially unsaturated. Cycloalkyl groups include groups having from 3 to 10 ring atoms (i.e. (C$_{3-10}$) cycloalkyl or C$_{3-10}$cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloheptyl, cyclooctyl, cyclononyl, cyclodecyl, norbornyl, and the like.

The term "fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

The term "halogen", as used herein, refers to fluorine, chlorine, bromine, or iodine, preferably iodine. In a preferred embodiment, the halogen substituent is iodine.

The terms "heteroalkyl," and "heteroalkenyl", as used herein, refer to optionally substituted alkyl and alkenyl radicals and which have one or more skeletal chain atoms selected from an atom other than carbon, e.g., oxygen, nitrogen, sulfur, phosphorus or combinations thereof. A numerical range may be given, e.g., C$_1$-C$_4$ heteroalkyl, which refers to the chain length in total, which in this example is 4 atoms long.

The terms "heteroaryl" or "heteroaromatic" or "HetAr" refers to a 5- to 18-membered aromatic radical (e.g., C$_5$-C$_{13}$heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene.

The term "stereoisomers" refers to compounds, which have identical chemical constitution, but differ with regard to the arrangement of the atoms or groups in space.

"Diastereomer" refers to a stereoisomer with two or more centers of chirality in which the compounds are not mirror images of one another. Diastereomers have different physical properties, e.g. melting points, boiling points, spectral properties, and chemical and biological reactivities. Mixtures of diastereomers may be separated under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McRaw-Hiff Dictionary of Chemical Terms* (1984), McGraw-Hill Book Company, New York; and Eliel, E. and Wilen, S., "Stereochemistry of Organic Compounds", John Wiley & Sons, Inc., New York, 1994.

The symbols (*), (#) and (§) in a chemical formula designates i) a point of attachment, ii) a radical, and/or iii) an unshared electron.

The term "antisense oligonucleotide (AON)," as used herein, refers to an oligonucleotide or oligomeric compound that is capable of interacting with and/or hybridizing to a pre-mRNA or an mRNA having a complementary nucleotide sequence thereby modifying gene expression.

The term "protecting group," as used herein, is intended to mean a group that selectively blocks one or more reactive sites in a multifunctional compound such that a chemical reaction can be carried out selectively on another unprotected reactive site and the group can then be readily removed or deprotected after the selective reaction is complete. A variety of protecting groups are disclosed, for example, in *Protecting Groups in Organic Synthesis*, T. W. Greene and P. G. M. Wuts, 3$^{rd}$ edition, John Wiley & Sons, New York 1999.

The terms "protecting group for an amino," "protecting group for an amino group," or "amino protecting group" as interchangeably used herein, are well known in the art and include those described in detail in *Protecting Groups in Organic Synthesis*, T. W. Greene and P. G. M. Wuts, 3$^{rd}$ edition, John Wiley & Sons, New York (1999), Greene's Protective Groups in Organic Synthesis, P. G. M. Wuts, 5$^{th}$ edition, John Wiley & Sons, (2014), and in *Current Protocols in Nucleic Acid Chemistry*, edited by S. L. Beaucage et al. June 2012, and hereby in particular in Chapter 2. Suitable "amino protecting groups" for the present invention include and are typically and preferably independently at each occurrence selected from methyl carbamate, ethyl carbamate, 9-fluorenylmethyl carbamate (Fmoc), 9-(2-sulfo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1,1-dimethyl-2,2-dibromoethyl carbamate (DB-t-BOC), 1,1-dimethyl-2,2,2-trichloroethyl carbamate (TCBOC), benzyl carbamate (Cbz), p-methoxybenzyl carbamate (Moz) and 2,4,6-trimethylbenzyl carbamate, (4-Methoxyphenyl) diphenylmethyl (MMTr); as well as formamide, acetamide, benzamide.

The terms "protecting group for a hydroxyl," "protecting group for a hydroxyl group," or "hydroxyl protecting group" as interchangeably used herein, are well known in the art and includes those described in detail in *Protecting Groups in Organic Synthesis*, T. W. Greene and P. G. M. Wuts, 3$^{rd}$ edition, John Wiley & Sons, New York (1999); Greene's Protective Groups in Organic Synthesis, P. G. M. Wuts, 5$^{th}$ edition, John Wiley & Sons, (2014), and in *Current Protocols in Nucleic Acid Chemistry*, edited by S. L. Beaucage et al. June 2012, and hereby in particular in Chapter 2. In a certain embodiment, the "hydroxyl protecting groups" of the present invention include and, typically and preferably are independently at each occurrence selected from, acetyl, benzoyl, benzyl, β-methoxyethoxymethyl ether (MEM), dimethoxytrityl, [bis-(4-methoxyphenyl)phenylmethyl] (DMTr), methoxymethyl ether (MOM), methoxytrityl [(4-methoxyphenyl)diphenylmethyl] (MMT), p-methoxybenzyl ether (PMB), methylthiomethyl ether, pivaloyl (Piv), tetrahydropyranyl (THP), tetrahydrofuran (THF), trityl (triphenylmethyl, Tr), silyl ether, such as t-Butyldiphenylsilyl ether (TBDPS), trimethylsilyl (TMS), tert-butyldimethylsilyl (TBDMS), tri-iso-propylsilyloxymethyl (TOM), and tri-isopropylsilyl (TIPS) ethers; methyl ethers, ethoxyethyl ethers (EE).

Preferred examples of the "hydroxyl protecting groups" of the present invention include and are independently at each occurrence selected from, acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4$^1$-dimethoxytrityl, trimethylsilyl, triethylsilyl, t-butyldimethylsilyl (TBDMS), t-butyldiphenylsilyl (TBDPS), triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, 4-monomethoxytrityl (MMTr), 4,4'dimethoxytrityl, (DMTr) and 4,4',4"-trimethoxytrityl (TMTr), 2-cyanoethyl (CE or Cne), 2-(trimethylsilyl)ethyl (TSE), 2-(2-nitrophenyl)ethyl, 2-(4-cyanophenyl)ethyl 2-(4-nitrophenyl)ethyl (NPE), 2-(4-nitrophenylsulfonyl)ethyl, 3,5-dichlorophenyl, 2,4-dimethylphenyl, 2-nitrophenyl, 4-nitrophenyl, 2,4,6-trimethylphenyl, 2-(2-nitrophenyl)ethyl, butylthiocarbonyl, 4,4',4"-tris(benzoyloxy)trityl, diphenylcarbamoyl, levulinyl, 2-(dibromomethyl)benzoyl (Dbmb), 2-(isopropylthiomethoxymethyl)benzoyl (Ptmt), 9-phenylxanthen-9-yl (pixyl) or 9-(p-methoxyphenyl)xanthine-9-yl (MOX).

The term "nucleobase," as used herein, and abbreviated as Bx, refers to unmodified or naturally occurring nucleobases as well as modified or non-naturally occurring nucleobases and synthetic mimetics thereof. A nucleobase is any heterocyclic base that contains one or more atoms or groups of atoms capable of hydrogen bonding to a heterocyclic base of a nucleic acid.

Typical and preferred examples of the nucleobase is a purine base or a pyrimidine base, wherein preferably said purine base is purine or substituted purine, and said pyrimidine base is pyrimidine or substituted pyrimidine. More preferably, the nucleobase is (i) adenine (A), (ii) cytosine (C), (iii) 5-methylcytosine (MeC), (iv) guanine (G), (v) uracil (U), or (vi) 5-methyluracil (MeU), or to a derivative of (i), (ii), (iii), (iv), (v) or (vi). The terms "derivative of" (i), (ii), (iii), (iv), (v) or (vi), and "nucleobase derivative" are used herein interchangeably. Derivatives of (i), (ii), (iii), (iv), (v) or (vi), and nucleobase derivatives, respectively, are known to the skilled person in the art and are described, for example, in Shainia V. K. et al., Med. Chem. Commun., 2014, 5, 1454-1471, and include without limitation 5-hydroxymethyl cytosine, xanthine, hypoxanthine, 2-aminoadenine, alkyl adenine, such as 6-methyl adenine, 2-propyl adenine, alkyl guanine, such as 6-methyl guanine, 2-propyl guanine, 2-thiouracil, 2-thiothymine and 2-thiocytosine, 5-halo uracil, 5-halo cytosine, alkynyl pyrimidine bases, such as 5-propynyl (—C≡C—CH$_3$) uracil, 5-propynyl (—C≡C—CH$_3$) cytosine, 6-azo uracil, 6-azo cytosine, 6-azo thymine, pseudo-uracil, 4-thiouracil; 8-substituted purine bases, such as 8-halo-, 8-amino-, 8-thiol-, 8-thioalkyl-, 8-hydroxyl-adenine or guanine, 5-substituted pyrimidine bases, such as 5-halo-, particularly 5-bromo-, 5-trifluoromethyl-uracil or -cytosine; 7-methylguanine, 7-methyladenine, 2-F-adenine, 2-amino-adenine, 8-azaguanine and 8-azaadenine, 7-deazaguanine, 7-deazaadenine, 3-deazaguanine, 3-deazaadenine, hydrophobic bases, promiscuous bases, size-expanded bases, or fluorinated bases. In certain embodiments, the nucleobase includes without limitation tricyclic pyrimidines, such as 1,3-diazaphenoxazine-2-one, 1,3-diazaphenothiazine-2-one or 9-(2-aminoethoxy)-1,3-diazaphenoxazine-2-one (G-clamp). The term "nucleobase derivative" also includes those in which the purine or pyrimidine base is replaced by other heterocycles, for example 7-deaza-adenine, 7-deazaguanosine, 2-aminopyridine or 2-pyridone. Further nucleobases of the invention include without limitation those known to skilled artisan (e.g. U.S. Pat. No. 3,687,808; Swayze et al., The Medicinal Chemistry of Oligonucleotides, in Antisense a Drug Technology, Chapter 6, pp. 143-182 (Crooke, S. T., ed., 2008); The Concise Encyclopedia Of Polymer Science And Engineering, Kroschwitz, J. I., Ed., John Wiley & Sons, 1990, pp. 858-859; Englisch et al., Angewandte Chemie, International Edition, 1991, Vol. 30 (6), pp. 613-623; Sanghvi, Y. S., Antisense Research and Applications, Crooke, S. T. and Lebleu, B., Eds., CRC Press, 1993, pp. 273-302). The term "nucleobase derivative" also includes those in which the purine or pyrimidine base is substituted with a moiety corresponding to the spacer of the present invention, in particular, for linking said one or more lipid moiety internally of said oligomeric compound, preferably said oligonucleotide. The specific linkages of said moiety corresponding to the spacer are known to the skilled person in the art. Preferred nucleobase derivatives include methylated adenine, guanine, uracil and cytosine and nucleobase derivatives, preferably of (i), (ii), (iii) or (iv), wherein the respective amino groups, preferably the exocyclic amino groups, are protected by acyl protecting groups or dialkylformamidino, preferably dimethylformamidino (DMF), and further include nucleobase derivatives such as 2-fluorouracil, 2-fluorocytosine, 5-bromouracil, 5-iodouracil, 2,6-diaminopurine, azacytosine and pyrimidine analogs such as pseudoisocytosine and pseudouracil. The preparation of modified nucleobases is known in the art and is described in U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594, 121; 5,596,091; 5,614,617; 5,645,985; 5,750,692; 5,830,653; 5,763,588; 6,005,096; and 5,681,941.

The term "internucleosidic linkage group," as used herein, refers to any linkage group known in the art that is able to link, preferably links, said tricyclo-deoxyribonucleic acid (tc-DNA) nucleoside either to a further tc-DNA nucleoside, a nucleoside other than a tc-DNA nucleoside, a non-nucleoside including a peptide, protein. Representative patents that teach such possible linkage groups are without limitation U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; 5,677,439; 5,646,269 and 5,792,608. The term "internucleosidic linkage group", thus, includes phosphorus linkage groups and non-phosphorus linkage groups. Non-phosphorus linkage groups do not contain a phosphorus atom and examples of non-phosphorus linkage groups include, and are typically and preferably selected from alkyl, aryl, preferably, phenyl, benzyl, or benzoyl, cycloalkyl, alkylenearyl, alkylenediaryl, alkoxy, alkoxyalkylene, alkylsulfonyl, alkyne, ether, each independently of each other optionally substituted with cyano, nitro, halogen; carboxyl, amide, amine, amino, imine, thiol, sulfide, sulfoxide, sulfone, sulfamate, sulfonate, sulfonamide, siloxane or mixtures thereof. Typically, and preferably, said internucleosidic linkage group is a phosphorus linkage group, and said phosphorus linkage group refers to a moiety comprising a phosphorus atom in the $P^{III}$ or $P^{V}$ valence state. Further preferably, said internucleosidic linkage group is a phosphorus linkage group. Again further preferably, said internucleosidic linkage group is selected from a phosphodiester linkage group, a phosphotriester linkage group, a phosphorothioate linkage group, a phosphorodithioate linkage group, a phosphonate linkage group, preferably a H-phosphonate linkage group or a methylphosphonate linkage group; a phosphonothioate linkage group, preferably a H-phosphonothioate linkage group, a methyl phosphonothioate linkage group; a phosphinate linkage group, a phosphorthioamidate linkage, a phosphoramidate linkage group, or a phosphite linkage group. In another very preferred embodiment, said internucleosidic linkage group is selected from a phosphodiester linkage group, a phosphotriester linkage group, a phosphorothioate linkage group, or a phosphonate linkage group, wherein the phosphonate is preferably a H-phosphonate linkage group or methylphosphonate linkage group.

As used herein, the term "nucleoside" refers to a compound comprising a nucleobase and a sugar covalently linked to said nucleobase. Further, the term "nucleoside" is meant to include all manner of naturally occurring or modified nucleosides or nucleoside mimetics that can be incorporated into an oligomer using natural or chemical oligomer synthesis. Typically and preferably, the term "nucleoside", as used herein, refers to a naturally occurring nucleoside, a modified nucleoside or nucleoside mimetic. The term "modified nucleosides" is intended to include modifications made to the sugar and/or nucleobase of a nucleoside as known to the skilled person in the art and described herein. The term "nucleoside mimetic" is intended to include those structures used to replace the sugar and the nucleobase. Examples of nucleoside mimetics include nucleosides wherein the nucleobase is replaced with a phenoxazine moiety (for example the 9-(2-aminoethoxy)-1, 3-diazaphenoxazine-2-one group) and the sugar moiety is replaced a cyclohexenyl or a bicyclo[3.1.0]hexyl moiety. The term "nucleoside" also includes combinations of modifications, such as more than one nucleobase modification, more than one sugar modification or at least one nucleobase and at least one sugar modification.

The sugar of the nucleoside includes without limitation a monocyclic, bicyclic or tricyclic ring system, preferably a tricyclic or bicyclic system or a monocyclic ribose or de(s)oxyribose. Modifications of the sugar further include but are not limited to modified stereochemical configurations, at least one substitution of a group or at least one deletion of a group. A modified sugar is typically and preferably a modified version of the ribosyl moiety as naturally occurring in RNA and DNA (i.e. the furanosyl moiety), such as bicyclic sugars, tetrahydropyrans, 2'-modified sugars, 3'-modified sugars, 4'-modified sugars, 5'-modified sugars, or 4'-substituted sugars. Examples of suitable sugar modifications are known to the skilled person and include, but are not limited to 2', 3' and/or 4' substituted nucleosides (e.g. 4'-S-modified nucleosides); 2'-O-modified RNA nucleotide residues, such as 2'-O-alkyl or 2'-O-(substituted)alkyl e.g. 2'-O-methyl, 2'-O-(2-cyanoethyl), 2'-O-(2-methoxyethyl (2'-MOE), 2'-O-(2-thiomethyl)ethyl; 2'-O-(haloalkoxy)methyl e.g. 2'-O-(2-chloroethoxy)methyl (MCEM), 2'-O-(2,2-dichloroethoxy)methyl (DCEM); 2'-O-alkoxycarbonyl e.g. 2'-O-[2-(methoxycarbonyl)ethyl] (MOCE), 2'-O-[2-(N-methylcarbamoyl)ethyl] (MCE), 2'-O-[2-(N,N-dimethylcarbamoyl)ethyl] (DMCE), in particular a 2'—O-methyl modification or a 2'—O-methoxyethyl (2'-O-MOE); or other modified sugar moieties, such as morpholino (PMO), cationic morpholino (PMOPlus) or a modified morpholino group, such as PMO-X. The term "PMO-X" refers to a modified morpholino group comprising at least one 3' or 5' terminal modification, such 3'-fluorescent tag, 3' quencher (e.g. 3'-carboxyfluorescein, 3'-Gene Tools Blue, 3'-lissamine, 3'-dabcyl), 3'-affinity tag and functional groups for chemical linkage (e.g. 3'-biotin, 3'-primary amine, 3'-disulfide amide, 3'-pyridyl dithio), 5'-end modifications (5'-primary amine, 5'-dabcyl), 3'-azide, 3'-alkyne, 5'-azide, 5'-alkyne, or as disclosed in WO2011/150408 and US2012/0065169.

"Bicylic sugar moieties" comprise two interconnected ring systems, e.g. bicyclic nucleosides wherein the sugar moiety has a 2'-O—CH(alkyl)-4' or 2'-O—CH$_2$-4' group, locked nucleic acid (LNA), xylo-LNA, alpha-L-LNA, beta-D-LNA, cEt (2'-O,4'-C constrained ethyl) LNA, cMOEt (2'-O,4'-C constrained methoxyethyl) LNA, ethylene-bridged nucleic acid (ENA), hexitol nucleic acid (HNA), fluorinated HNA (F-HNA), pyranosyl-RNA (p-RNA), or 3'-deoxypyranosyl-DNA (p-DNA).

In a preferred embodiment, the oligomeric compound is an oligonucleotide. The term "oligonucleotide," as used herein, refers to a compound comprising at least two nucleosides linked to each other each by a internucleosidic linkage group. Thus, the term "oligonucleotide," as used herein, includes, and typically and preferably refer to, oligomeric compounds comprising at least two nucleosides linked by internucleosidic linkage groups, wherein said at least two nucleosides are independently selected from naturally occurring nucleosides, modified nucleosides or nucleoside mimetics.

The oligomeric compound can be single stranded or double stranded. In one embodiment, the oligomeric compound is double stranded (i.e. a duplex). In a preferred embodiment, the oligomeric compound is single stranded.

The term "terminus" refers to the end or terminus of the oligomeric compound, wherein the integer (3', 5', etc.) indicates to the carbon atom of the sugar included in the nucleoside of the oligomeric compound. The term "5' terminal group" or "3' terminal group," as used herein, refers to a group located at the 5' terminus or 3' terminus, respectively.

The term "natural" or "naturally occurring," as interchangeably used herein, refers to compounds that are of natural origin.

The term "complementary" refers to a nucleic acid molecule that can form hydrogen bond(s) with another nucleic acid molecule by either traditional Watson-Crick base pairing or other non-traditional types of pairing (e.g., Hoogsteen or reversed Hoogsteen hydrogen bonding) between complementary nucleosides or nucleotides. "Complementary" (or "specifically hybridizable") are terms that indicate a sufficient degree of complementarity or precise pairing such that stable and specific binding occurs between an oligomeric compound and a pre-mRNA or mRNA target. It is understood in the art that a nucleic acid molecule need not be 100% complementary to a target nucleic acid sequence to be specifically hybridizable. That is, two or more nucleic acid molecules may be less than fully complementary. Complementarity may be indicated by a percentage of contiguous residues in a nucleic acid molecule that can form hydrogen bonds with a second nucleic acid molecule. For example, if a first nucleic acid molecule has 10 nucleotides and a second nucleic acid molecule has 10 nucleotides, then base pairing of 5, 6, 7, 8, 9, or 10 nucleotides between the first and second nucleic acid molecules represents 50%, 60%, 70%, 80%, 90%, and 100% complementarity, respectively. "Perfectly" or "fully" complementary nucleic acid molecules means those in which all the contiguous residues of a first nucleic acid molecule will hydrogen bond with the same number of contiguous residues in a second nucleic acid molecule, wherein the nucleic acid molecules either both have the same number of nucleotides (i.e., have the same length) or the two molecules have different lengths.

The term "exon skipping" refers to the modification of pre-mRNA splicing by the targeting of splice donor and/or acceptor sites within a pre-mRNA with one or more complementary antisense oligonucleotides or oligomeric compounds. By blocking access of a spliceosome to one or more splice donor or acceptor sites, or any other site within an exon or intron involved in the definition of splicing, an oligonucleotide can prevent a splicing reaction and cause the deletion of exons from a fully-processed mRNA. Exon skipping is achieved in the nucleus during the maturation process of pre-mRNAs. Exon skipping includes the masking of key sequences involved in the splicing of targeted exons by using antisense oligonucleotides that are complementary to splice donor sequences within a pre-mRNA. For example, the inventive compositions comprising said oligomeric compounds provided herein may be suitably employed for exon skipping through the masking of splice sites at intron/exon junctions within a dystrophin pre-mRNA thereby facilitating the deletion of a mutant exon during the processing of the pre-mRNA to a mature mRNA.

The term "exon inclusion" refers to oligonucleotide-mediated processes such as the base-pairing of antisense oligonucleotides to a target pre-mRNA to block an exonic or intronic splicing enhancer and block the corresponding splicing repressor and/or disrupt an unfavorable secondary structure, resulting in more efficient recognition of the exon by the spliceosome and restoration of exon expression.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the human subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit in a human subject. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable salt" refers to salts derived from a variety of organic and inorganic counter ions known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid and phosphoric acid. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts, preferably said pharmaceutically acceptable salt is the sodium salt.

In case of hydroxyl groups (OH) or thiol groups (SH) typically and preferably bound to P(III) or P(V) and present in said one or more lipid moiety, typically and preferably as part of the group B of said one or more lipid moiety, or present in said spacer, or present in said oligomeric compound, preferably in said oligonucleotide, of the present invention, as part of said internucleosidic linkage group, typically and preferably selected from phosphorothioate or phosphorodiester, each of said hydroxyl groups (OH) or thiol groups (SH) can independently of each other be present as said OH group or in its ionic state such as the O-anion and a pharmaceutically acceptable cation, or as said SH group or in its ionic state such as the S-anion and a pharmaceutically acceptable cation. Further included are any combinations and any states of equilibrium between the aforementioned situations in the inventive compositions, in particular taking further oxygen or sulfur-containing groups on said P(III) or P(V) such as (=O), (=S), another OH or SH group, into account, which is known by the skilled person in the art. For sake of simplicity, in the aspects and embodiments of the present invention, typically only one of the aforementioned situations is described. By way of example, a preferred spacer of the present invention is indicated herein as #-NH—C$_{2-12}$alkylene-OP(O)(SH)-§. Included herein is, as indicated without limitation, the spacer where the hydrogen is located at the oxygen, thus, #—NH-C$_{2-12}$alkylene-OP(OH)(S)-§ and all of the pharmaceutically acceptable salt thereof.

Thus, a pharmaceutically acceptable salt in the context of hydroxyl groups (OH) and or thiol groups (SH) typically and preferably bound to P(III) or P(V) and present in said one or more lipid moiety, typically and preferably as part of the group B of said one or more lipid moiety, or present in said spacer, or present in said oligomeric compound, preferably in said oligonucleotide, of the present invention, as part of said internucleosidic linkage group, typically and preferably selected from phosphorothioate or phosphorodiester, refers to the inventive compositions in which one or more of said OH groups or said SH groups are independently of each other be present as said OH group or in its ionic state such as the O-anion and a pharmaceutically acceptable cation thereof, or as said SH group or in its ionic state such as the S-anion and a pharmaceutically acceptable cation, and wherein typically and preferably said pharmaceutically acceptable cation is selected from protonated trimethylamine, protonated diethylamine, protonated methylamine, ammonium, sodium or potassium, further preferably wherein said pharmaceutically acceptable cation is sodium.

"Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}$C- or $^{14}$C-enriched carbons, are within the scope of this invention.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable minor images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (5)-isomer and 20% (R)-isomer, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or Pirkle's reagents, or derivatization of a compounds using a chiral compound such as Mosher's acid followed by chromatography or nuclear magnetic resonance spectroscopy.

In preferred embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., Enantiomers, Racemates and Resolutions, Wiley Interscience, New York (1981); E. L. Eliel, Stereochemistry of Carbon Compounds, McGraw-Hill, New York (1962); and E. L. Eliel and S. H. Wilen, Stereochemistry of Organic Compounds, Wiley-Interscience, New York (1994).

The terms "enantiomerically enriched" and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (5)-enantiomer relative to the (R)-enantiomer, such as at least 75% by weight, or such as at least 80% by weight. In some embodiments, the enrichment can be significantly greater than 80% by weight, providing a "substantially enantiomerically enriched" or a "substantially non-racemic" preparation, which refers to preparations of compositions which have at least 85% by weight of one enantiomer relative to other enantiomer, such as at least 90% by weight, or such as at least 95% by weight. The terms "enantiomerically pure" or "substantially enantiomerically pure" refers to a composition that comprises at least 98% of a single enantiomer and less than 2% of the opposite enantiomer.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Unless, more particularly defined herein, "substituted" means that the referenced group may have attached one or more additional groups, radicals or moieties individually and independently selected from, for example, acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfonyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons. The term "optionally substituted" means optional substitution with the specified groups, radicals or moieties.

Compounds of the invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

When ranges are used herein to describe, for example, physical or chemical properties such as molecular weight or chemical formulae, all combinations and sub-combinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, from 0% to 10%, from 0% to 5% of the stated number or numerical range.

tc-DNA Nucleoside Precursors

In an embodiment, the invention includes a process for preparing a tc-DNA nucleoside precursor of Formula I, Formula II, Formula III, Formula IV, Formula V, or Formula VI:

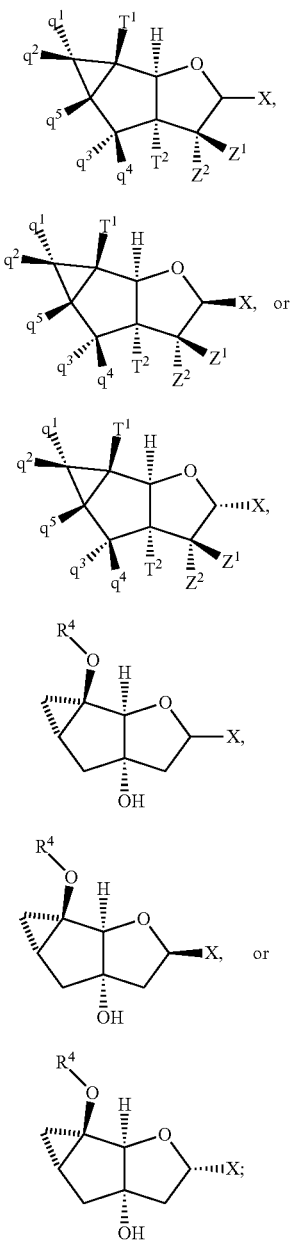

wherein X may be alkoxy;

$T^1$ and $T^2$ may each be $OR^1$, where $R^1$ is H or a hydroxyl protecting group;

$q^1, q^2, q^3, q^4$, and $q^5$ are each independently selected from the group consisting of hydrogen, halogen, $C_{1-6}$alkyl, $C_{2-6}$alkenyl, $C_{2-6}$alkynyl, substituted $C_{1-6}$alkyl, substituted $C_{2-6}$alkenyl, substituted $C_{2-6}$alkynyl, and $(CH_2)_n$—C(O)—$R^2$, wherein n is 0 to 6 and wherein $R^2$ is selected from the group consisting of OH, $NH_2$, O—$C_{1-32}$lkyl and NH—$C_{1-32}$alkyl;

$R^4$ may be is a hydroxyl protecting group; and $z^1$ and $z^2$ are each independently selected from the group consisting of hydrogen, $C_{1-6}$alkyl, $C_{1-6}$alkoxyl, O—$C_{2-6}$alkenyl, O—$C_{2-6}$alkynyl, substituted $C_{1-6}$alkyl, substituted $C_{1-6}$alkoxy, substituted O—$C_{2-6}$alkenyl, and substituted O—$C_{2-6}$alkynyl halogen.

In some embodiments, $T^1$ is $OR^1$ and $R^1$ is a hydroxyl protecting group. In some embodiments, each hydroxyl protecting group is independently selected from the group consisting of acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl⁻(TBDMS), t-butyldiphenylsilyl (TBDPS), triphenylsilyl, triisopropylsilyl, benzoylformate, chloroacetyl, trichloroacetyl, trifiuoroacetyl, pivaloyl, 9-fluorenylmethyl carbonate, mesylate, tosylate, triflate, 4-monomethoxytrityl (MMTr), 4,4'dimethoxytrityl, (DMTr) and 4,4',4''-trimethoxytrityl (TMTr), 2-cyanoethyl (CE or Cne), 2-(trimethylsilyl)ethyl (TSE), 2-(2-nitrophenyl)ethyl, 2-(4-cyanophenyl)ethyl 2-(4-nitrophenyl)ethyl (NPE), 2-(4-nitrophenylsulfonyl)ethyl, 3,5-dichlorophenyl, 2,4-dimethylphenyl, 2-nitrophenyl, 4-nitrophenyl, 2,4,6-trimethylphenyl, 2-(2-nitrophenyl)ethyl, butylthiocarbonyl, 4,4',4''-tris(benzoyloxy)trityl, diphenylcarbamoyl, levulinyl, 2-(dibromomethyl)benzoyl (Dbmb), 2-(isopropylthiomethoxymethyl)benzoyl (Ptmt), 9-phenylxanthen-9-yl (pixyl), and 9-(p-methoxyphenyl)xanthine-9-yl (MOX). In some embodiments, the hydroxyl protecting group is TBDMS.

In some embodiments, $q^1$, $q^2$, $q^3$, $q^4$, and/or $q^5$ are hydrogen.

In some embodiments, $z^1$ and/or $z^2$ are hydrogen.

In some embodiments, $T^2$ is $OR^1$ and $R^1$ is H. In some embodiments, $T^2$ is hydroxy.

In some embodiments, X is $OR^3$, wherein $R^3$ is methyl, ethyl, propyl, isopropyl, butyl, isobutyl, tert-butyl, pentyl, or hexyl. In some embodiments, $R^3$ is methyl. In some embodiments, X is methoxy.

In some embodiments, $R^4$ is TBDMS.

In an embodiment, the invention includes a process for preparing a tc-DNA nucleoside precursor of Formula VII, Formula VIII, or Formula IX:

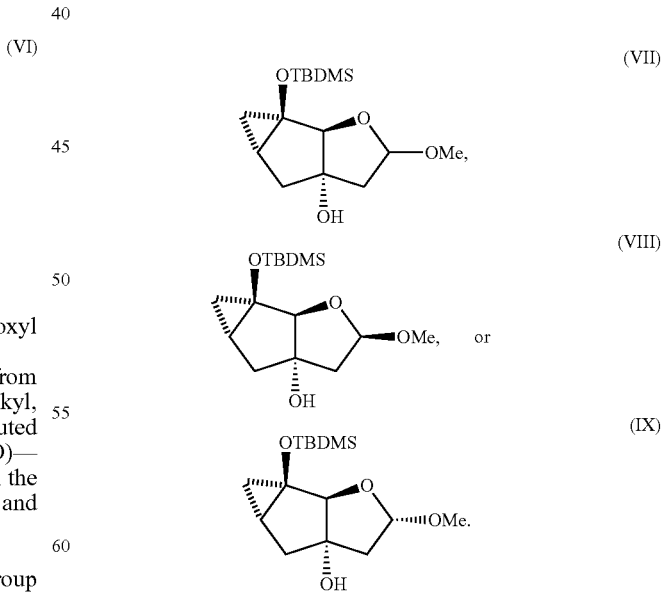

The tc-DNA nucleoside precursors of Formulas I-IX may be used in the production of tc-DNA nucleosides, which include a nucleobase, and are useful in the manufacture of antisense oligonucleotide therapies.

Preparation of tc-DNA Nucleoside Precursors

In an embodiment, the tc-DNA nucleoside precursors described herein (e.g., a compound of Formulas I-IX) may be prepared according to one or more of the following processes.

In an embodiment, the invention includes a method of preparing a tc-DNA nucleoside precursor of any one of Formulas I-IX, the method comprising the steps of:
a. preparing a carbene precursor at a carbene preparation temperature;
b. adding a compound of Formula X, Formula XI, or Formula XII:

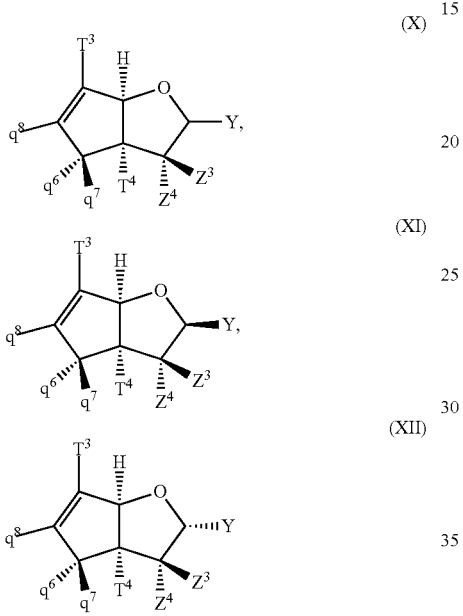

(X)

(XI)

(XII)

to the carbene precursor at a cyclopropanation temperature; and
c. providing the tc-DNA nucleoside precursor of one of Formulas I-IX,
wherein Y is alkoxy;
$T^3$ and $T^4$ may be $OR^5$, where $R^5$ is H or a hydroxyl protecting group;
$q^6$, $q^7$, and $q^8$ are each independently selected from the group consisting of hydrogen, halogen, $C_{1-6}$alkyl, $C_{2-6}$alkenyl, $C_{2-6}$alkynyl, substituted $C_{1-6}$alkyl, substituted $C_{2-6}$alkenyl, substituted $C_{2-6}$alkynyl, and $(CH_2)_n$—C(O)—$R^6$, wherein n is 0 to 6 and wherein $R^6$ is selected from the group consisting of OH, $NH_2$, O—$C_{1-32}$lkyl and NH—$C_{1-32}$alkyl; and
$z^3$ and $z^4$ are each independently selected from the group consisting of hydrogen, $C_{1-6}$alkyl, $C_{1-6}$alkoxyl, O—$C_{2-6}$alkenyl, O—$C_{2-6}$alkynyl, substituted $C_{1-6}$alkyl, substituted $C_{1-6}$alkoxy, substituted O—$C_{2-6}$alkenyl, and substituted O—$C_{2-6}$alkynyl halogen.

In an embodiment, the invention includes a method of preparing a tc-DNA nucleoside precursor of any one of Formulas I-IX, the method comprising the steps of:
a. preparing a carbene precursor at a carbene preparation temperature;
b. preparing a solution of a compound of Formula X, Formula XI, or Formula XII:

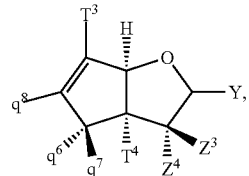

(X)

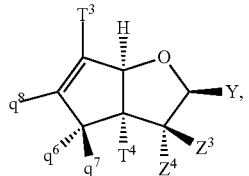

(XI)

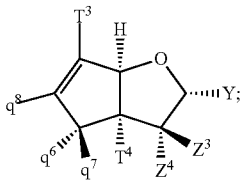

(XII)

c. adding the carbene precursor to the solution of the compound of Formula X, Formula XI, or Formula XII, at a cyclopropanation temperature; and
d. providing the tc-DNA nucleoside precursor of one of Formulas I-IX,
wherein Y is alkoxy;
$T^3$ and $T^4$ may be $OR^5$, where $R^5$ is H or a hydroxyl protecting group;
$q^6$, $q^7$, and $q^8$ are each independently selected from the group consisting of hydrogen, halogen, $C_{1-6}$alkyl, $C_{2-6}$alkenyl, $C_{2-6}$alkynyl, substituted $C_{1-6}$alkyl, substituted $C_{2-6}$alkenyl, substituted $C_{2-6}$alkynyl, and $(CH_2)_n$—C(O)—$R^6$, wherein n is 0 to 6 and wherein $R^6$ is selected from the group consisting of OH, $NH_2$, O—$C_{1-32}$alkyl and NH—$C_{1-32}$alkyl; and
$z^3$ and $z^4$ are each independently selected from the group consisting of hydrogen, $C_{1-6}$alkyl, $C_{1-6}$alkoxyl, O—$C_{2-6}$alkenyl, O-$C_{2-6}$alkynyl, substituted $C_{1-6}$alkyl, substituted $C_{1-6}$alkoxy, substituted O—$C_{2-6}$alkenyl, and substituted O—$C_{2-6}$alkynyl halogen.

In an embodiment, the methods may include the step of adding a Lewis acid catalyst to the mixture of the compound of Formula X, Formula XI, or Formula XII and the carbene precursor. In some embodiments, the Lewis acid catalyst may be selected from the group consisting of $Et_2AlCl$, $Et_2Zn$, $ZnI_2$, $ZnCl_2$, $ZnBr_2$, $Ti(OiPr)_4$, $Me_2AlCl$, TMSOTf, $TiCl_4$, and combinations thereof.

In an embodiment, the step of preparing the carbene precursor may include combining a Lewis acid catalyst (e.g., $Et_2Zn$) and $R^7I_2$ in a solvent. In some embodiments, $R^7$ may be selected from the group consisting of $CH_2$, CH—$C_{1-6}$alkyl, CH—$C_{2-6}$alkenyl, CH—$C_{2-6}$alkynyl, substituted CH—$C_{1-6}$alkyl, substituted CH—$C_{2-6}$alkenyl, substituted CH—$C_{2-6}$alkynyl, and CH—$(CH_2)_n$—C(O)—$R^8$, wherein n is 0 to 6 and wherein $R^8$ is selected from the group consisting of OH, $NH_2$, O—$C_{1-32}$lkyl and NH—$C_{1-32}$alkyl. In some embodiments, $R^7$ is alkyl. In some embodiments, $R^7$ is $CH_2$.

In some embodiments, the step of preparing the carbene precursor may include combining a carbene additive, a Lewis acid catalyst (e.g., $ZnEt_2$), and $R^7I_2$, in any order. In some embodiments, the step of preparing the carbene precursor may include adding a carbene additive to the mixture of a Lewis acid catalyst (e.g., $ZnEt_2$) and $R^7I_2$.

In some embodiments, the carbene additive may be an aliphatic alcohol (e.g, substituted or unsubstituted alkyl alcohol), an aromatic alcohol (e.g., substituted or unsubstituted phenol), a substituted or unsubstituted carboxylic acid (e.g., trichloroacetic acid), or a substituted or unsubstituted phosphate (e.g., $(alkyl-O)_2P(O)OH$ or $(aryl-O)_2P(O)OH$). In some embodiments, the carbene additive may be a substituted carboxylic acid of the formula $Q_3CCO_2H$, wherein each Q may be independently selected from the group consisting of H, Cl, Br, and F. In some embodiments, the carbene additive may be a substituted carboxylic acid of the formula $Q_3CCO_2H$, wherein $Q_3C$ may be defined as $CCl_3$, $CHCl_2$, $CH_2CL$, or $CF_3$. In some embodiments, the carbene additive may be a substituted alkyl alcohol of the formula $Q_3CCH_2OH$, wherein each Q may be independently selected from the group consisting of H, Cl, Br, and F. In some embodiments, the carbene additive may be a substituted carboxylic acid of the formula $Q_3CCH_2OH$, wherein $Q_3C$ may be defined as $CCl_3$, $CHCl_2$, $CH_2Cl$, or $CF_3$. In some embodiments, the carbene additive may be trichloroacetic acid, 2,2,2-trifluoroethanol, thrichlorophenol, or $(n-BuO)_2P(O)OH$.

In some embodiments, the solvent may comprise hexanes, toluene, dichloromethane ($CH_2Cl_2$), tetrahydrofuran (THF), acetonitrile ($CH_3CN$), dimethylformamide (DMF), diethylether, dimethoxyethane (DME), or a combination thereof. In some embodiments, the solvent is dichloromethane, DME, or a combination thereof. In some embodiments, the solvent may be a polar aprotic solvent. In some embodiments, the polar aprotic solvent may comprise, dichloromethane ($CH_2Cl_2$), tetrahydrofuran (THF), acetonitrile ($CH_3CN$), dimethylformamide (DMF), diethylether, dimethoxyethane (DME), or a combination thereof.

In some embodiments, the carbene precursor is $Q_3CCO_2ZnR^7I$, $Q_3CCH_2OZnR^7I$, $(n-BuO)_2P(O)OZnR^7I$, $(alkyl-O)_2P(O)OZnR^7I$, $(aryl-O)_2P(O)OZnR^7I$, or $2,4,6-Cl_3C_6H_2OZnR^7I$, wherein each Q may be independently selected from the group consisting of H, Cl, Br, and F. In some embodiments, the carbene precursor is $Q_3CCO_2ZnR^7I$, $Q_3CCH_2OZnR^7I$, $(n-BuO)_2P(O)OZnR^7I$, $(alkyl-O)_2P(O)OZnR^7I$, $(aryl-O)_2P(O)OZnR^7I$, or $2,4,6-Cl_3C_6H_2OZnR^7I$, wherein $Q_3C$ may be defined as $CCl_3$, $CHCl_2$, $CH_2Cl$, or $CF_3$. In some embodiments, the carbene precursor is $CCl_3CO_2ZnR^7I$, $CF_3CH_2OZnR^7I$, $(n-BuO)_2P(O)OZnR^7I$, or $2,4,6-Cl_3C_6H_2OZnR^7I$. In some embodiments, the carbene precursor is $CCl_3CO_2ZnCH_2I$, $CF_3CH_2OZnCH_2I$, $(n-BuO)_2P(O)OZnCH_2I$, or $2,4,6-Cl_3C_6H_2OZnCH_2I$.

In some embodiments, the step of preparing the solution of the compound of Formula X, Formula XI, or Formula XII, may include adding $ZnEt_2$ to the compound of Formula X, Formula XI, or Formula XII.

In some embodiments, the carbene preparation temperature may be a temperature selected from the range of about −80° C. to about 0° C. In some embodiments, the carbene preparation temperature may be about −80° C. to about 0° C. In some embodiments, the carbene preparation temperature may be greater than −80, −79, −78, −77, −76, −75, −74, −73, −72, −71, −70, −69, −68, −67, −66, −65, −64, −63, −62, −61, −60, −59, −58, −57, −56, −55, −54, −53, −52, −51, −50, −49, −48, −47, −46, −45, −44, −43, −42, −41, −40, −39, −38, −37, −36, −35, −34, −33, −32, −31, −30, −29, −28, −27, −26, −25, −24, −23, −22, −21, −20, −19, −18, −17, −16, −15, −14, −13, −12, −11, −10, −9, −8, −7, −6, −5, −4, −3, −2, −1, −0° C. In some embodiments, the carbene preparation temperature may be less than −80, −79, −78, −77, −76, −75, −74, −73, −72, −71, −70, −69, −68, −67, −66, −65, −64, −63, −62, −61, −60, −59, −58, −57, −56, −55, −54, −53, −52, −51, −50, −49, −48, −47, −46, −45, −44, −43, −42, −41, −40, −39, −38, −37, −36, −35, −34, −33, −32, −31, −30, −29, −28, −27, −26, −25, −24, −23, −22, −21, −20, −19, −18, −17, −16, −15, −14, −13, −12, −11, −10, −9, −8, −7, −6, −5, −4, −3, −2, −1, −0° C. In some embodiments, the carbene preparation temperature may be about −80, −79, −78, −77, −76, −75, −74, −73, −72, −71, −70, −69, −68, −67, −66, −65, −64, −63, −62, −61, −60, −59, −58, −57, −56, −55, −54, −53, −52, −51, −50, −49, −48, −47, −46, −45, −44, −43, −42, −41, −40, −39, −38, −37, −36, −35, −34, −33, −32, −31, −30, −29, −28, −27, −26, −25, −24, −23, −22, −21, −20, −19, −18, −17, −16, −15, −14, −13, −12, −11, −10, −9, −8, −7, −6, −5, −4, −3, −2, −1, −0° C.

In some embodiments, the carbene preparation temperature may include a first carbene preparation temperature and a second carbene preparation temperature, where the temperature of the reaction begins at the first carbene preparation temperature and increases to the second carbene preparation temperature, wherein the first carbene preparation temperature is less than the second carbene preparation temperature. In some embodiments, however, the temperature of the reaction begins at the first carbene preparation temperature and is decreased to the second carbene preparation temperature, wherein the first carbene preparation temperature is greater than the second carbene preparation temperature.

In some embodiments, the cyclopropanation temperature may be a temperature selected from the range of about −30° C. to about room temperature (i.e., 25° C.). In some embodiments, the cyclopropanation temperature may be about −30° C. to about room temperature (i.e., 25° C.). In some embodiments, the cyclopropanation temperature may be greater than −30, −29, −28, −27, −26, −25, −24, −23, −22, −21, −20, −19, −18, −17, −16, −15, −14, −13, −12, −11, −10, −9, −8, −7, −6, −5, −4, −3, −2, −1, −0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30° C. In some embodiments, the cyclopropanation temperature may be less than −30, −29, −28, −27, −26, −25, −24, −23, −22, −21, −20, −19, −18, −17, −16, −15, −14, −13, −12, −11, −10, −9, −8, −7, −6, −5, −4, −3, −2, −1, −0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30° C. In some embodiments, the cyclopropanation temperature may be about −30, −29, −28, −27, −26, −25, −24, −23, −22, −21, −20, −19, −18, −17, −16, −15, −14, −13, −12, −11, −10, −9, −8, −7, −6, −5, −4, −3, −2, −1, −0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30° C.

In some embodiments, the cyclopropanation temperature may include a first cyclopropanation temperature and a second cyclopropanation temperature, where the temperature of the reaction begins at the first cyclopropanation temperature and increases to the second cyclopropanation temperature, wherein the first cyclopropanation temperature is less than the second cyclpropanation temperature. In some embodiments, however, the temperature of the reaction begins at the first cyclopropanation temperature and is decreased to the second cyclopropanation temperature, wherein the first cyclopropanation temperature is greater than the second cyclopropanation temperature.

In some embodiments of the methods described herein, the carbene precursor added to the compound of Formula X, Formula XI, or Formula XII an amount of about 1.0 to about 10 molar equivalents of the carbene precursor to the compound of Formula X, Formula XI, or Formula XII.

In some embodiments of the methods described herein, the carbene precursor added to the compound of Formula X, Formula XI, or Formula XII an amount of less than 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5, 6, 7, 8, 9, or 10 molar equivalents of the carbene precursor to the compound of Formula X, Formula XI, or Formula XII.

In some embodiments of the methods described herein, the carbene precursor added to the compound of Formula X, Formula XI, or Formula XII an amount of greater than 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5, 6, 7, 8, 9, or 10 molar equivalents of the carbene precursor to the compound of Formula X, Formula XI, or Formula XII.

In some embodiments of the methods described herein, the carbene precursor added to the compound of Formula X, Formula XI, or Formula XII an amount of about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5, 6, 7, 8, 9, or 10 molar equivalents of the carbene precursor to the compound of Formula X, Formula XI, or Formula XII.

tc-DNA Nucleosides Prepared from tc-DNA Nucleoside Precursors

In an embodiment, tc-DNA nucleosides may be prepared from the tc-DNA nucleoside precursors described herein.

In an embodiment, the invention includes a method of preparing a compound of Formula XIII, Formula XIV, or Formula XV from one or more of the tc-DNA nucleoside precursors of Formulas I to IX:

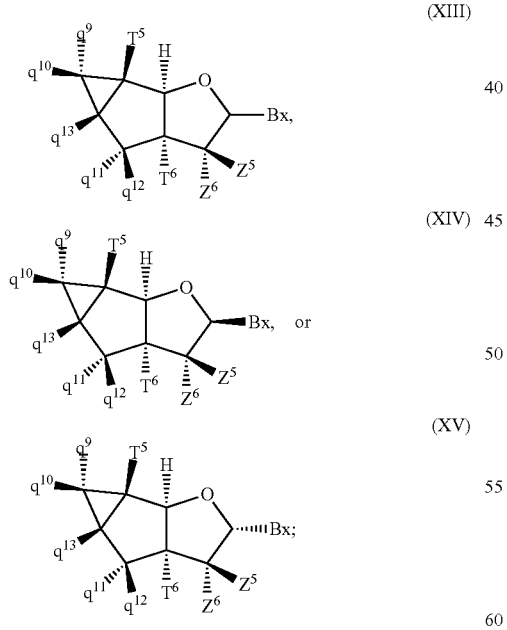

wherein Bx is a nucleobase;
one of $T^5$ and $T^6$ is an internucleosidic linkage group, and the other of $T^5$ and $T^6$ is $OR^9$, $OR^{10}$, a 5' terminal group, a 3' terminal group or a internucleosidic linkage group, wherein $R^9$ is H or a hydroxyl protecting group, and $R^{10}$ is a phosphorus moiety;

$q^9$, $q^{10}$, $q^{11}$, $q^{12}$ and $q^{13}$ are each independently selected from the group consisting of hydrogen (H), halogen, $C_{1-6}$alkyl, $C_{2-6}$alkenyl, $C_{2-6}$alkynyl, substituted $C_{1-6}$alkyl, substituted $C_{2-6}$alkenyl, substituted $C_{2-6}$alkynyl, and $(CH_2)_n$—C(O)—$R^{11}$, wherein n is 0 to 6 and wherein $R^{11}$ is selected from the group consisting of OH, $NH_2$, O—$C_{1-32}$lkyl and NH—$C_{1-32}$alkyl; and $z^5$ and $z^6$ are each independently selected from the group consisting of H, halogen, $C_{1-6}$alkyl, $C_{1-6}$alkoxyl, O—$C_{2-6}$alkenyl, O—$C_{2-6}$alkynyl, substituted $C_{1-6}$alkyl, substituted $C_{1-6}$alkoxy, substituted O—$C_{2-6}$alkenyl, and substituted O—$C_{2-6}$alkynyl.

In an embodiment, the tc-DNA nucleosides described herein comprise a compound of Formula XIII, Formula XIV, or Formula XV, wherein Bx is selected from the group consisting of thymine, adenine, guanine, and cytosine. In an embodiment, the tc-DNA nucleosides described herein comprise a compound of Formula XIII, Formula XIV, or Formula XV, wherein Bx is a modified base. In an embodiment, the tc-DNA nucleosides described herein comprise a compound of Formula XIII, Formula XIV, or Formula XV, wherein Bx is a modified base selected from the group consisting of 5-methylcytosine, 5-bromouracil, inosine, and 2,6-diaminopurine.

In an embodiment, the invention includes tc-DNA nucleoside-containing oligomeric compounds comprising one or more tc-DNA nucleosides of the Formula XIII, Formula, XIV, Formula XV, or a pharmaceutically acceptable salt thereof.

While preferred embodiments of the invention are shown and described herein, such embodiments are provided by way of example only and are not intended to otherwise limit the scope of the invention. Various alternatives to the described embodiments of the invention may be employed in practicing the invention.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1

Preparation of a Bicyclo Sugar Precursor

Intermediate 10 may be prepared according to the synthetic route depicted in FIG. 1 starting from D-Mannose.

Example 2

Preparation of a Bicyclo Sugar Precursor

Figure 2:
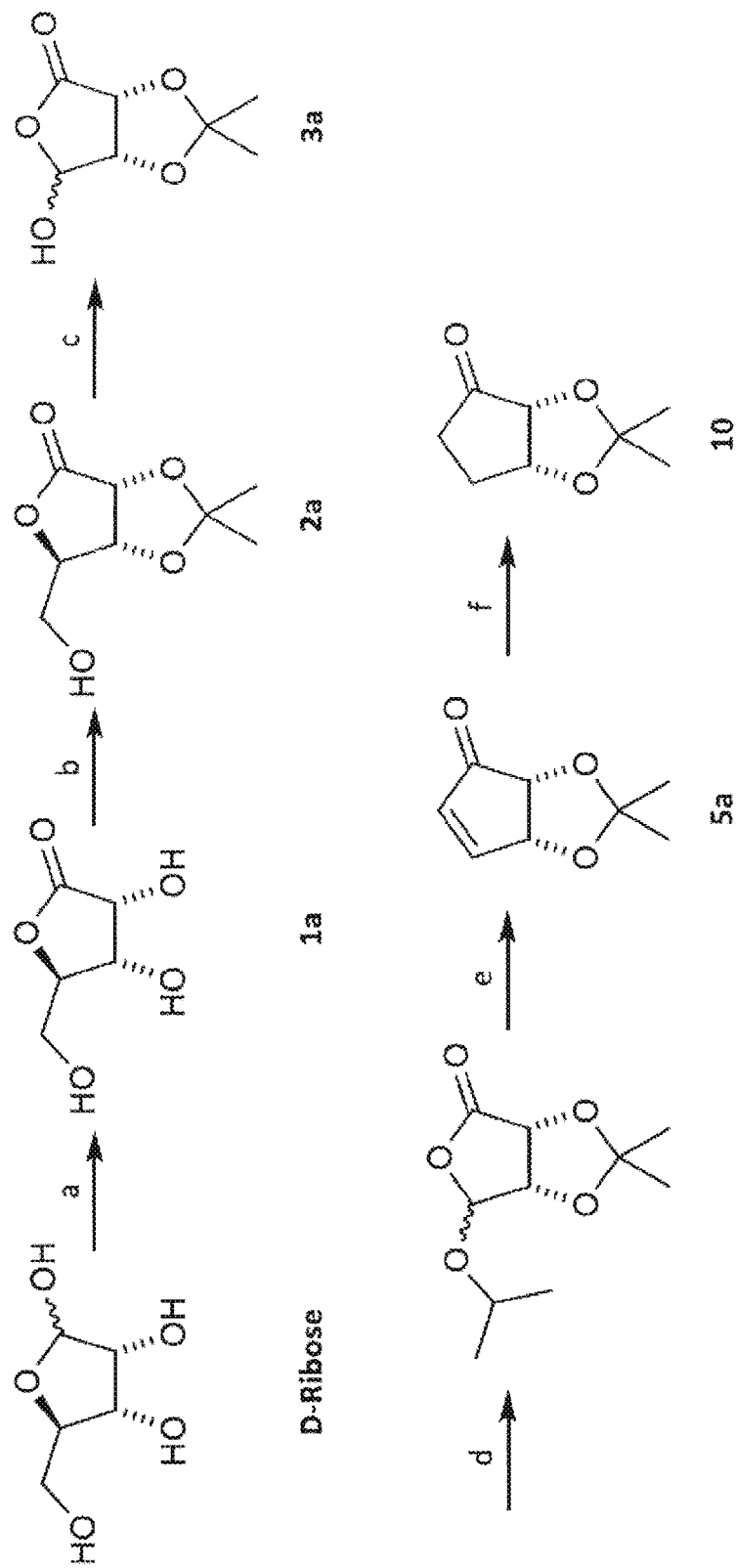
FIG. 2 illustrates an alternative synthetic route to the bicyclo sugar intermediate 10 from D-Ribose. The reagents and conditions used in the synthetic route are as follows: (a) Br$_2$ (1.04 eq.), NaHCO$_3$ (2 eq.), H$_2$O, 0-5° C., crude; (b) DMP, acetone, H$_2$SO$_4$ (cat.), Amberlyst, rt, (crystallization, 67% yield over two steps); (c) NaIO$_4$ (1.05 eq.), NaOH (1.1 eq.), 0° C., BaCl$_2$ (crude, 78% yield); (d) iPrOH, PPTS (0.02 eq.), reflux (chromatography, 63% yield); (e) LiCH$_2$(O)P(OMe)$_2$ (1.1 eq.), THF, −78° C. to rt (crude, ca. 60% yield); and (f) 10% Pd/C, H$_2$, EtOAc, rt (chromatography, 95% yield). 16% yield from D-Ribose over 6 steps.

Intermediate 10 may be prepared according to the alternative synthetic route depicted in FIG. 2 starting from D-Ribose.

Example 3

Preparation of a tert-Butyldimethylsilyl Enol Ether Intermediate

Figure 3:
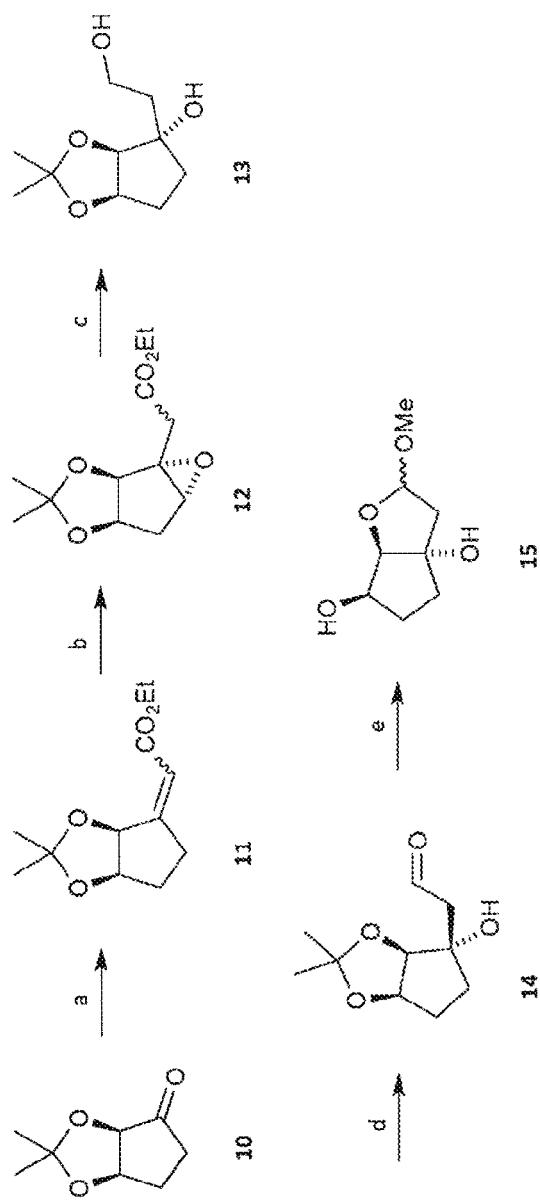
FIG. 3 illustrates a synthetic route to an alcohol intermediate 15 from intermediate 10. The reagents and conditions used in the synthetic route are as follows: (a) (EtO)$_2$P(O)CH$_2$CO2Et (1 eq.), THF, 0° C. to rt, 88% yield; (b) MCPBA (2.2 eq.), CH$_2$Cl$_2$, 0 to 40° C., 18 h; (c) LiAlH$_4$ (1.5 eq.), THF, 0° C. to rt, 1 h (chromatography, 86% yield); (d) IBX, THF/DMSO, rt, 2.5 h, 91% yield; and (e) MeOH, Amberlite IR-120 (H$^+$), 16 h at rt then 60° C. for 2 h (chromatography, 77% yield).
Figure 4:
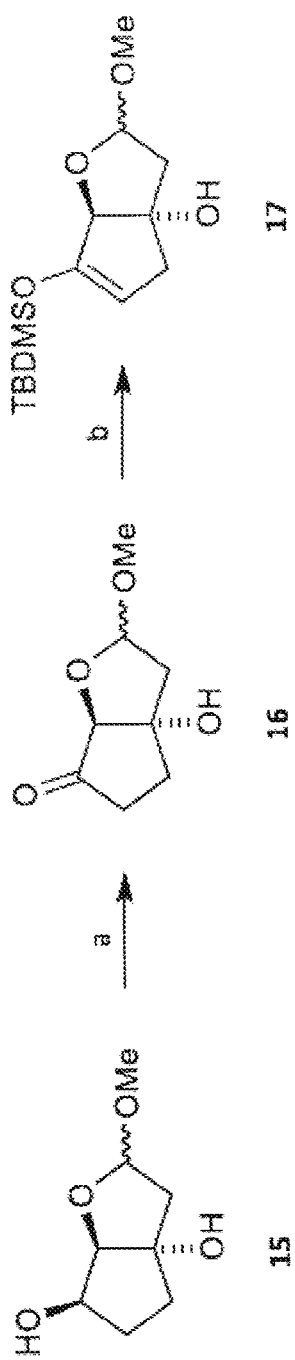
FIG. 4 illustrates a synthetic route to a tert-butyldimethylsilyl enol ether intermediate 17. The reagents and conditions used in the synthetic route are as follows: (a) TCCA (0.35 eq.), TEMPO (0.007 eq.), AcONa (3 eq.), CH$_2$Cl$_2$, Acetone, −15 to 0° C., 1 h; and (b) TBDMSCl (1.4 eq.), DBU (1.6 eq.), KI (0.1 eq.), THF, rt, 2 h. Alternatively, reagents and conditions used in the synthetic route may be: (a) DMP, CH$_2$Cl$_2$, rt; and (b) (1) LDA, −65° C., then (2) TBDMSCl, THF, −65° C. to 0° C.

Silyl enol ether 17 may be prepared from intermediate 10 according to the synthetic routes depicted in FIGS. 3 and 4.

Example 4

Cyclopropanation of Compound 17 with Carbenoid Prepared from CH$_2$I$_2$ and Et$_2$Zn in the Absence of Additives According to the following scheme, compound 17 was converted to tc-DNA Nucleoside Precursor 18 using the cyclopropanation conditions set forth in Examples 4 to 7:

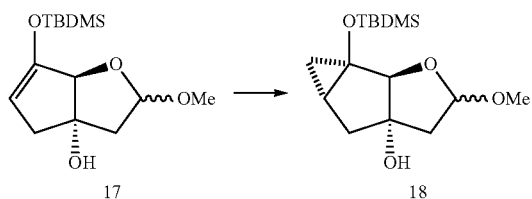

1.07 g purified α-anomer (3.736 mmol) 17 was dissolved in 37 ml of dry CH$_2$Cl$_2$ and cooled to 0° C. (ice). Subsequently, 22.3 ml (22.3 mmol, 6 eq.) Et$_2$Zn 1.0 M in hexane (Aldrich) were added dropwise and stirred under Ar for 30 min at 0° C. Then, 3.02 ml (37.2 mmol, 10 eq.) of CH$_2$I$_2$ were added dropwise over 15 min at the same temperature and stirred for further 2 h at 0° C. Afterwards the cooling bath was removed and the mixture was stirred for additional 21 h at ambient temperature. TLC showed substantial amount of unreacted α-17. It was diluted by addition of EtOAc and quenched with 50 mL of sat. aqueous NH$_4$Cl. Extractive work-up provided 1.79 g of crude which was purified by chromatography on silica-gel giving 0.43 g (39%) of 18 and 0.49 g of mixture of compound 17 and 18 (approximately 20:80).

Example 5

Cyclopropanation of Compound 17 with Carbene Prepared from CH$_2$I$_2$ and Activated Zn AgOAc (60 mg) was dissolved in conc. AcOH (60 ml) at 70° C. and Zn (10 g; grain size ca. 0.5 mm, shortly corroded with 0.1M HCl, washed with H$_2$O and EtOH, and dried at r.t./0.01 Torr for 15 min) was added at once. The mixture was stirred for 1 min, decanted, and washed with AcOH (40 ml) and dry Et$_2$O (3×40 ml). The now dark grey Ag-Zn couple was stored over Ag-wool in abs. Et$_2$O. To the Ag-Zn couple (6.3 g, 96.4 mmol) in Et$_2$O (11 ml), CH$_2$I$_2$ (8.41 g, 31.4 mmol) was added through a syringe, and the mixture was stirred under Ar for 1 h at r.t. A solution of 17 (1.5 g, 5.23 mmol, mixture of both anomers) in dry Et$_2$O (11 ml) was added dropwise to the carbene solution. Within 10 min, and the mixture was refluxed under Ar for 3 h. The grey suspension was then cooled to 0° C. and diluted with Et$_2$O (30 ml) before pyridine (6.6 ml) was added dropwise at 0° C. The white precipitate was filtered off over Celite, the filtrate washed with sat. NaHCO$_3$ (2×50 ml), and the aq. phases extracted with Et$_2$O (50 ml). The combined org. phase was dried (MgSO$_4$), evaporated, and the residue purified by flash chromatography (silica gel (50 g), Et$_2$O/hexane 1:1), providing 908 mg (58%) of compound 18 in a ratio of 2:1 (α/β; $^1$H-NMR) as a colorless oil.

Example 4

Cyclopropanation of Compound 17 with Stable Carbenoid Prepared from CH$_2$I$_2$ and Et$_2$Zn and (n-BuO)$_2$P(O)OH Preparation of the (n-BuO)$_2$P(O)OZnCH$_2$I Solution To 8 ml toluene at −10° C. (dry ice/acetone), 2.4 ml (2.4 mmol) diethylzinc 1.0 M in toluene (Acros) were added dropwise. Subsequently, 0.5 ml (0.53 g, 2.44 mmol) (n-BuO)$_2$P(O)OH 97% (Aldrich) diluted with 5 ml of toluene were added dropwise slowly. The mixture was stirred for 20 min at −10° C. under Ar. Then, 0.20 ml (0.65 g, 2.44 mmol) CH$_2$I$_2$ (Alfa Aesar) were added dropwise and stirred for 30 min at −10° C. under Ar. The clear solution was stored in the freezer.

Crude, unpurified compound 17 was dissolved in reaction solvent and mixed with the solution of carbenoid (n-BuO)$_2$P(O)OZnCH$_2$I prepared according to procedure described above at r.t. Mixture was stirred for time given in Table 1 followed by aqueous work up by extraction. Yields, if indicated are after FC.

Examples given in Table 1 demonstrate that unpractically long reaction times and excess of carbenoid is necessary to complete the reaction.

TABLE 1

| | Cyclopropanation Conditions in the Absence of Lewis Acid | | | | | |
|---|---|---|---|---|---|---|
| Exp. | Conc. of s.m. | Eq. of [Zn] | Temp. | Solvent | Time | Notes |
| 1 | 0.022M | 7 eq | RT | DCM/PhCH$_3$, hex | 8 d | Mixture of 17 and 18, yiled ca 10% |
| 2 | 0.008M | 25 eq | RT | DCM/PhCH$_3$, hex | 7 d | Reaction complete |
| 3 | 0.008M | 25 eq | 40° C. | DCM/PhCH$_3$, hex | 1 h + 8 h RT | Reaction complete |
| 4 | 0.042M | 5 eq | 40° C. | DCM/PhCH$_3$ | 48 h | Reaction not complete, extensive decomposition, yield ca 81% |
| 5 | 0.042M | 5 eq | RT | DCM/PhCH$_3$ | 48 h | Reaction not complete, extensive decomposition, yield ca 38% |

Example 5

Cyclopropanation of Compound 17 with Stable Carbenoid Prepared from $CH_2I_2$ and $Et_2Zn$ and $(n-BuO)_2P(O)OH$ in Various Solvents Preparation of the $(n-BuO)_2P(O)OZnCH_2I$ Solution Carbenoid prepared according to a procedure described above, the toluene was replaced by $CH_2Cl_2$ where indicated. Diethylzinc 1.0 M in toluene (Acros) was used in all experiments.

Crude, unpurified compound 17 was dissolved in reaction solvent and mixed with the solution of carbenoid $(n-BuO)_2P(O)OZnCH_2I$ prepared according to procedure described above at r.t. Mixture was stirred for time given in Table 2 at 0-10° C. followed by aqueous work up by extraction. The ratio of 17/18 was evaluated from 1H NMR of the crude.

Examples given in Table 2 demonstrate the scope of solvents for cyclopropanation, the conversion of 17 was incomplete regardless of the solvent.

TABLE 2

Cyclopropanation Conditions in the Absence of Lewis Acid, Effect of Solvent

| Exp. No. | Solvent carbene | Solvent s.m. | Ratio 17/18 (NMR) | notes |
|---|---|---|---|---|
| 1 | Toluene | $CH_2Cl_2$ | 60:40 | 5 eq carbenoid, RT overnight |
| 2 | Toluene | $CH_2Cl_2$ | 63:37 | 5 eq carbenoid, 0° C. |
| 3 | Toluene | Hexane | 69:31 | 5 eq carbenoid, 0° C., 48 h |
| 4 | Toluene | Toluene | 72:28 | 5 eq carbenoid, 0° C., 48 h |
| 5 | Toluene | $Et_2O$ | 71:29 | 5 eq carbenoid, 0° C., 48 h |
| 6 | Toluene | THF | 74:26 | 5 eq carbenoid, 0° C., 48 h |
| 8 | $CH_2Cl_2$ | $CH_2Cl_2$ | 61:39 | 5 eq carbenoid, 0° C., 48 h |

Example 6

Cyclopropanation of Compound 17 with Stable Carbenoid Prepared from $CH_2I_2$ and $Et_2Zn$ and $(n-BuO)_2P(O)OH$ in Various Solvents Preparation of the $(n-BuO)_2P(O)OZnCH_2I$ Solution Diethylzinc (1.5 M in toluene, 14.0 ml, 20.95 mmol) (Acros) was added dropwise to solution of 4.3 ml of $(n-BuO)_2P(O)OH$ (4.54 g, 20.95 mmol, 97%, Aldrich) in 22.8 ml $CH_2Cl_2$ at −20° C. (dry ice/acetone) during 30 min. The mixture was stirred for 30 min at −20° C. under Ar. Then, 1.69 ml (5.61 g, 20.95 mmol) $CH_2I_2$ (Alfa Aesar) were added dropwise and stirred for 30 min at −20° C. under Ar. The clear solution was stored in the freezer.

Crude, unpurified compound 17 (0.272 g, 0.70 mmol) was dissolved in reaction solvent and Lewis acid indicated in Table 3 was added at 0° C. (ice bath). The mixture was stirred for 15 mi at the same temperature. Then solution of carbenoid $(n-BuO)_2P(O)OZnCH_2I$ prepared according to procedure described above was added at the same temperature. Mixture was stirred for time given in Table 3 at 0-10° C. followed by aqueous work up by extraction. The ratio of 17/18 was evaluated from 1H NMR of the crude.

Examples given in Table 3 demonstrate the acceleration of cyclopropanation of compound 17 in the presence of Lewis acids

TABLE 3

Cyclopropanation Conditions in the Absence Presence of Lewis Acid

| Exp. No. | Solvent carbene | Solvent s.m. | Additive/amount | Ratio 17/18 (NMR) | notes |
|---|---|---|---|---|---|
| 1 | Toluene | Toluene | $Et_2Zn$/0.5 eq | 75:75 | 2.5 eq carbenoid, 0° C., 48 h |
| 2 | Toluene | Toluene | $Et_2Zn$/1 eq | 65:35 | 2.5 eq carbenoid, 0° C., 48 h |
| 3 | Toluene | Toluene | $Et_2Zn$, $ZnI_2$/0.5 eq each | 73:27 | 2.5 eq carbenoid, 0° C., 48 h |
| 4 | $CH_2Cl_2$ | $CH_2Cl_2$ | $ZnI_2$/0.2 eq | 87:13 | 2 eq carbenoid, 0° C., 48 h |
| 5 | $CH_2Cl_2$ | $CH_2Cl_2$ | $ZnCl_2$/0.2 eq | 94:6 | 1.5 eq carbenoid, 0° C., 48 h |
| 6 | $CH_2Cl_2$ | $CH_2Cl_2$ | $ZnBr_2$/0.2 eq | 90:10 | 2 eq carbenoid, 0° C., 48 h |
| 7 | $CH_2Cl_2$ | $CH_2Cl_2$ | $Ti(OiPr)_4$/0.2 eq | 92:8 | 2 eq carbenoid, 0° C., 48 h |
| 8 | $CH_2Cl_2$ | $CH_2Cl_2$ | $Et_2Zn$/1 eq, $Me_2AlCl$ 0.2 eq | ca. 50:50 | 2 eq carbenoid, 0° C., 24 h |
| 9 | $CH_2Cl_2$ | $CH_2Cl_2$ | TMSOTf/0.2 eq | Decomp. | 2 eq carbenoid, 0° C., 24 h |
| 10 | $CH_2Cl_2$ | $CH_2Cl_2$ | TMSOTf/1 eq | Decomp. | 2 eq carbenoid, 0° C., 24 h |
| 11 | $CH_2Cl_2$ | $CH_2Cl_2$ | $TiCl_4$/0.2 eq | Decomp. | 2 eq carbenoid, 0° C., 24 h |
| 12 | $CH_2Cl_2$ | $CH_2Cl_2$ | $TiCl_4$/1 eq | Decomp. | 2 eq carbenoid, 0° C., 24 h |
| 13 | $CH_2Cl_2$ | $CH_2Cl_2$ | $TiCl_4$/0.1 eq, $Ti(OiPr)_4$/0.1 eq | 85:15 | 2 eq carbenoid, 0° C., 24 h |
| 14 | $CH_2Cl_2$ | $CH_2Cl_2$ | $TiCl_4$/0.5 eq, $Ti(OiPr)_4$/0.5 eq | Decomp. | 2 eq carbenoid, 0° C., 24 h |
| 15 | $CH_2Cl_2$ | $CH_2Cl_2$ | $Et_2Zn$/1 eq, $Me_2AlCl$ 0.2 eq | 18% | 2 eq carbene, 0° C. to RT, 5 d, seems to have bit less byproduct |
| 16 | $CH_2Cl_2$ | $CH_2Cl_2$ | $Et_2Zn$/1 eq, $TiCl_4$ 0.2 eq | 15% | 2 eq carbene, 0° C. to RT, 5 d |

Example 7

Preparation of a tc-DNA Nucleoside Precursor

TABLE 4

Cyclopropanation Conditions

| Exp. No. | Carbene Precursor/ Carbenoid | Reaction Conditions | Yield of 18 (after Chromatography) | Notes |
|---|---|---|---|---|
| 1 | $CCl_3CO_2ZnCH_2I$ | $ZnEt_2$, $CH_2Cl_2$, $-40°$ C., 1 h; then trichloroacetic acid, DME, $CH_2Cl_2$, $-15°$ C., 1 h; then purified 17 ($\alpha/\beta$ 1:1), $CH_2Cl_2$, rt, 21 h | — | 2 eq. $ZnEt_2$, 4 eq. $CH_2I_2$, 0.2 eq. $CCl_3CO_2H$, 1 eq. DME (traces of $\alpha$-17 not converted) |
| 2 | $CCl_3CO_2ZnCH_2I$ | $ZnEt_2$, $CH_2I_2$, $CH_2Cl_2$, $-40°$ C., 1 h; then trichloroacetic acid, DME, $CH_2Cl_2$, $-15°$ C., 1 h; then purified 17 ($\alpha/\beta$ 1:1), $CH_2Cl_2$, rt, 3 h | — | 3 eq. $ZnEt_2$, 6 eq. $CH_2I_2$, 0.25 eq. $CCl_3CO_2H$, 1 eq. DME ($\alpha$-17 not converted completely) |
| 3 | $CCl_3CO_2ZnCH_2I$ | $ZnEt_2$, trichloroacetic acid, $CH_2Cl_2$, $-20°$ C., 20 min; then $CH_2I_2$, $-10°$ C., 15 min; then purified 17 ($\alpha/\beta$ 1.08:1), $CH_2Cl_2$, rt, 3 h | 46% $\beta$-anomer | 3 eq. $ZnEt_2$, 3 eq. $CH_2I_2$, 3 eq. $CCl_3CO_2H$ (traces of $\alpha$-17 not converted) |
| 4 | $CF_3CH_2OZnCH_2I$ + Lewis Acid | $ZnEt_2$, $CH_2I_2$, $CH_2Cl_2$, $-78°$ C. up to $-15°$ C., 1 h; then 2,2,2-Trifluoroethanol, $CH_2Cl_2$, $-15°$ C., 40 min; then purified 17 ($\alpha/\beta$ 1:1), $CH_2Cl_2$, $-15°$ C., 15 min; then 0.3 eq. $Et_2AlCl$, rt, 21 h | 48% $\beta$-anomer | 3 eq $ZnEt_2$, 6 eq. $CH_2I_2$, 3 eq. Trifluoroethanol (traces $\alpha$-17 not converted) |
| 5 | $(n-BuO)_2P(O)OZnCH_2I$ + Lewis Acid | Purified 17 ($\alpha/\beta$ 1:1), $Et_2Zn$ (1 eq.), $CH_2Cl_2$, $-10°$ C., 10 min; then $(n-BuO)_2P(O)OZnCH_2I$-solution, $-10°$ C., 10 min; then $Et_2AlCl$, $-10°$ C. up to rt, 21 h. | — | 2.1 eq. carbenoid, 0.5 eq. $Et_2AlCl$ ($\alpha$ and $\beta$ 17 did not convert completely) |
| 6 | $(n-BuO)_2P(O)OZnCH_2I$ + Lewis Acid | Purified 17 ($\alpha/\beta$ 1:1), $Et_2Zn$ (1 eq.), $CH_2Cl_2$, $-10°$ C., 10 min; then $(n-BuO)_2P(O)OZnCH_2I$-solution, $-10°$ C., 10 min; then $Et_2AlCl$, $-10°$ C. up to rt, 24 h. | 77.1% (q-NMR) 1:1 mixture of the two diastereomers | 3 eq. carbenoid, 0.5 eq. $Et_2AlCl$; Zn-impurities no separated (traces of $\alpha$-17 not converted) |
| 7 | $(n-BuO)_2P(O)OZnCH_2I$ + Lewis Acid | Purified 17 ($\alpha/\beta$ 1.2:1), $Et_2Zn$ (1 eq.), $CH_2Cl_2$, $-10°$ C., 10 min; then $(n-BuO)_2P(O)OZnCH_2I$-solution, $-10°$ C., 10 min; then $Et_2AlCl$, $-10°$ C. up to rt, 21 h. | — | 2.2 eq. carbenoid, 1 eq. $Et_2AlCl$ ($\alpha$ and $\beta$ 17 not converted completely) |
| 8 | $2,4,6-Cl_3C_6H_2OZnCH_2I$ | 2,4,6-Trichlorophenol, $Et_2Zn$, $CH_2Cl_2$, $-10°$ C., 15 min; then $CH_2I_2$, $-10°$ C., 15 min; then purified 17 ($\alpha/\beta$ 1:1), $CH_2Cl_2$, rt, 20 h | 62.8% (q-NMR) $\beta$-anomer | 3 eq. Trichlorophenol, 3 eq. $Et_2Zn$, 3 eq. $CH_2I_2$ (traces of $\alpha$-17 not converted) |
| 9 | $(n-BuO)_2P(O)OZnCH_2I$ + Lewis Acid | Purified $\alpha$-17, $Et_2Zn$ (1 eq.), $CH_2Cl_2$, $-10°$ C., 10 min; then $(n-BuO)_2P(O)OZnCH_2I$-solution, $-10°$ C., 10 min; then $Et_2AlCl$, $-10°$ C., 25 h | 69.7% (q-NMR) $\alpha$-anomer | 3 eq. carbenoid, 0.5 $Et_2AlCl$; Zn impurities not separated (almost no traces of unconverted $\alpha$-17) |

Preparation of the $(n-BuO)_2P(O)OZnCH_2I$ Solution

To 22.8 ml $CH_2Cl_2$ at $-20°$ C. (dry ice/acetone), 14.0 ml (20.95 mmol) diethylzinc 1.5 M in toluene (Acros) were added dropwise. Subsequently, 4.28 ml (4.54 g, 20.95 mmol) $(n-BuO)_2P(O)OH$ 97% (Aldrich) were added dropwise slowly. The mixture was stirred for 30 min at $-20°$ C. under Ar. Then, 1.69 ml (5.62 g, 20.95 mmol) $CH_2I_2$ (Reagent Plus, 99%, Aldrich) were added dropwise and stirred for 30 min at $-15°$ C. under Ar. The clear solution was stored in the freezer.

Experiment 5—Cyclopropanation of Compound 17 with 2.1 Molar Eqs. of Carbene and 0.5 Eqs. of Lewis Acid 181 mg purified $\alpha$- and 174 mg $\beta$-anomer (355 mg, 1.239 mmol) 17 were dissolved in 0.7 ml $CH_2Cl_2$ and cooled to $-10°$ C. (dry ice). Subsequently, 826 µl (1.239 mmol, 1 eq.) $Et_2Zn$ 1.5 M in toluene (Acros) were added dropwise and stirred under Ar for 10 min at $-10°$ C. Then, 5.312 ml (2.602 mmol, 2.1 eq.) $(n-BuO)_2P(O)OZnCH_2I$ solution were added dropwise and stirred for further 10 min at $-10°$ C. Subsequently, 336 µl (298.5 mg, 0.619 mmol, 50 mol-%) diethylaluminum chloride solution 25 wt.-% in toluene (Aldrich) were added dropwise slowly. The mixture was stirred for 2 h at −10° C. and was then allowed to warm slowly in the bath to room temperature. The mixture was stirred for a total of 21 hours.

Experiment 6—Cyclopropanation of Compound 17 with 3 Molar Eqs. of Carbene and 0.5 Eqs. of Lewis Acid Purified α-(106 mg) and anomer (105 mg) (211 mg, 0.737 mmol) 17 were dissolved in 0.5 ml CH$_2$Cl$_2$ and cooled to −10° C. Subsequently, 491 µl (0.737 mmol, 1 eq.) Et$_2$Zn 1.5 M in toluene were added dropwise and stirred for 10 min at −10° C. Then, 4.51 ml (2.211 mmol, 3 eq.) (n-BuO)$_2$P(O)OZnCH$_2$I solution were added dropwise and stirred for further 10 min at −10° C. Subsequently, 201 µl (0.369 mmol, 50 mol-%) diethylaluminum chloride solution 25 wt.-% in toluene were added dropwise slowly. The mixture was stirred under Ar for 2 h at −10° C. and then for 22 h at rt. The mixture was quenched with 4 ml saturated NH$_4$Cl solution, taken up in MTBE and washed with 30 ml saturated NaCl solution. The aqueous phase was extracted with 2×20 ml MTBE. The combined organic phases were dried over Na$_2$SO$_4$, filtered and concentrated as well as dried via high vacuum for a short time. The resulting yellowish oil was purified by flash chromatography via 20 g silica gel with Hex/EtOAc 3:1. 225 mg (~0.749 mmol, 102%) of a 1:1 diastereoisomeric mixture compound 18 resulted, according to $^{31}$P-NMR contaminated with "dibutyl phosphate" in form of a yellowish oil.

$^1$H-q-NMR (24.4 mg prod., 24.9 mg dimethyl terephthalate, 2 ml CD$_3$CH): turbid solution with white precipitate→after the addition of 150 µl pyridine, a clear solution with white precipitate is formed.

Experiment 7—Cyclopropanation of Compound 17 with 2.2 Molar Eqs. of Carbene and 0.5 Eqs. of Lewis Acid Purified α-(117 mg) and β-anomer (100 mg) (217 mg, 0.758 mmol) 17 were dissolved in 0.5 ml CH$_2$Cl$_2$ and cooled to −10° C. Subsequently, 505 µl (0.758 mmol, 1 eq.) Et$_2$Zn 1.5 M in toluene were added dropwise and stirred for 10 min at −10° C. Then, 3.40 ml (1.668 mmol, 2.2 eq.) (n-BuO)$_2$P(O)OZnCH$_2$I solution were added dropwise and stirred for further 10 min at −10° C. Subsequently, 412 µl (0.758 mmol, 1 eq.) diethylaluminum chloride solution 25 wt.-% in toluene were added dropwise slowly. The mixture was stirred under Ar for 2 h at −10° C. and then for 19 h at rt.

Experiment 9—Cyclopropanation of Compound 17 with 3 Molar Eqs. of Carbene and 0.5 Eqs. of Lewis Acid 211 mg (0.737 mmol) purified α anomer 17 were dissolved in 0.5 ml CH$_2$Cl$_2$ and cooled to −10° C. Subsequently, 491 µl (0.737 mmol, 1 eq.) Et$_2$Zn 1.5 M in toluene were added dropwise and stirred for 10 min at −10° C. Then, 6.01 ml (2.211 mmol, 3 eq.) (n-BuO)$_2$P(O)OZnCH$_2$I solution were added dropwise and stirred for further 10 min at −10° C. Subsequently, 201 µl (0.369 mmol, 50 mol-%) diethylaluminum chloride solution 25 wt.-% in toluene were added dropwise slowly. The mixture was stirred under Ar for 2 h at −10° C. and then for 23 h at rt (→ yellowish solution). 202 mg (~0.672 mmol, 91%) of the a anomer of compound 18 resulted, according to $^{31}$P-NMR contaminated with "dibutyl phosphate", in faun of a yellowish oil.

$^1$H-q-NMR (37.38 mg product, 37.24 mg dimethyl terephthalate, 1 ml CDCl$_3$).

Precipitation of Zn salts: 158 mg contaminated compound 18, 2 ml CH$_3$CN, and 200 µl (2.47 mmol) pyridine were combined. The mixture was stirred for 1 h at rt and for 1 h at 0° C. Precipitate was filtered off with Celite, washed with cold CH$_3$CN and the filtrate was concentrated (pyridine with toluene co-evaporated) as well as dried overnight via high vacuum. 146 mg of compound 18 resulted Example 8

Preparation of a tc-DNA Nucleoside Precursor

A 1.5 M solution of Et$_2$Zn in Toluene (51.49 ml, 77.24 mmol, 5 eq.; Acros) was added dropwise over 7 minutes to dry CH$_2$Cl$_2$ (19.17 ml) at −20° C. Subsequently Dibutyl phosphate 97% (12.63 ml, 61.79 mmol, 4 eq.; Aldrich) was added dropwise over a period of 12 minutes (exothermic reaction, temp. increases from −20° C. to −10° C.). After being stirred for 30 min, Diiodomethane (4.98 ml, 61.79 mmol, 4 eq.; Aldrich, 99%) was added dropwise over 3 minutes and the mixture was stirred for another 30 min at −20° C. Next a solution of crude 17 (5.0 g, purity 88.5%, 15.45 mmol, 1 eq.) in dry CH$_2$Cl$_2$ (10.51 ml) was added dropwise (exothermic reaction, temp. increases from −20° C. to −10° C.). After being stirred for 15 min at −20° C., Et$_2$AlCl (25 wt. % solution in Toluene, 4.20 ml, 7.72 mmol, 0.5 eq.; Aldrich) was added. The reaction mixture was stirred for 2 h at −10° C. Subsequently the cooling bath was removed and the mixture was allowed to warm up spontaneously to room temperature and stirred at that temperature for 22 h. Afterwards it was diluted with Hexane (400 ml) and washed with 0.2 M aq. HCl (2×400 ml). The combined aqueous phases were re-extracted with Hexane (300 ml). Afterwards the combined organic phases were washed with 0.2 M aq. NaOH (2×400 ml), dried over Na$_2$SO$_4$, filtered and evaporated to yield 5.09 g of TC-003 (mixture of two anomers with ratio 24:76, purity by $^1$H-q-NMR 73.5%, yield 81%) as a dark yellow, viscous liquid.

We claim:
1. A method of preparing a tc-DNA nucleoside precursor of any one of Formulas I-III:

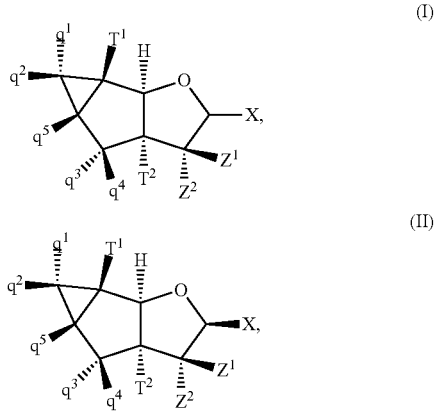

-continued

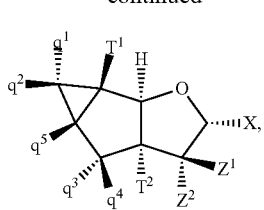
(III)

the method comprising the steps of:
a. preparing a carbene precursor at a carbene preparation temperature, wherein the step of preparing the carbene precursor comprises combining a first Lewis acid and $R^7I_2$ in a solvent, wherein $R^7$ is selected from the croup consisting of $CH_2$, CH—$C_{1-6}$alkyl, CH—$C_{2-6}$alkenyl, CH—$C_{2-6}$alkynyl, substituted CH—$C_{1-6}$alkyl, substituted CH—$C_{2-6}$alkenyl, substituted CH—$C_{2-6}$alkynyl, and CH-$(CH_2)_n$—C(O)-$R^8$, wherein n is 0 to 6 and wherein $R^8$ is selected from the croup consisting of OH, $NH_2$, O-$C_{1-32}$alkyl and NH-$C_{1-32}$alkyl;
b. mixing the carbene precursor with a compound of Formula X, Formula XI, or Formula XII:

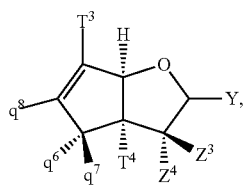
(X)

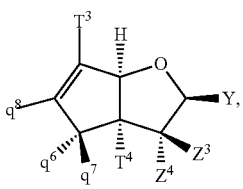
(XI)

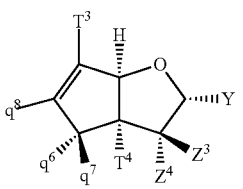
(XII)

at a cyclopropanation temperature; and
c. adding a catalytic amount of a second Lewis acid to the mixture;
wherein X and Y are each alkoxy;
$T^1$, $T^2$, $T^3$ and $T^4$ are each $OR^5$, where each $R^5$ is H or a hydroxyl protecting group;
$q^5$, $q^6$, and $q^7$, and $q^8$ are each independently selected from the group consisting of hydrogen, halogen, $C_{1-6}$alkyl, $C_{2-6}$alkenyl, $C_{2-6}$alkynyl, substituted $C_{1-6}$alkyl, substituted $C_{2-6}$alkenyl, substituted $C_{2-6}$alkynyl, and —$(CH_2)_n$—C(O)-$R^6$, wherein n is 0 to 6 and wherein $R_6$ is selected from the group consisting of OH, $NH_2$, O-$C_{1-32}$alkyl and NH-$C_{1-32}$alkyl;
$q^8$ is selected from the group consisting of hydrogen, halogen, $C_{1-3}$alkyl, $C_2$-3alkenyl, $C_{2-3}$alkynyl, substituted $C_{1-3}$alkyl, substituted $C_{2-3}$alkenyl, substituted $C_{2-3}$alkynyl, and —$(CH_2)_n$—C(O)—$R^6$, wherein n is 0 to 2 and wherein $R^6$ is selected from the group consisting of OH, $NH_2$, O-$C_{1-3}$alkyl and NH-$C_{1-3}$alkyl; and
$z^3$ and $z^4$ are each independently selected from the group consisting of hydrogen, $C_{1-6}$alkyl, $C_{1-6}$alkoxyl, O-$C_{2-6}$alkenyl, O-$C_{2-6}$alkynyl, substituted $C_{1-6}$alkyl, substituted $C_{1-6}$alkoxy, substituted O-$C_{2-6}$alkenyl, and substituted O-$C_{2-6}$alkynyl halogen.

2. The method of claim 1, wherein the tc-DNA nucleoside precursor is any one of Formulas IV-IX:

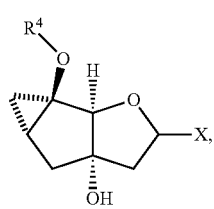
(IV)

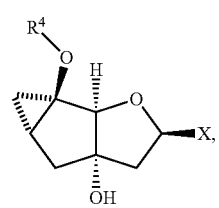
(V)

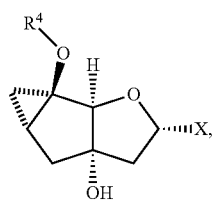
(VI)

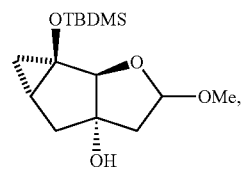
(VII)

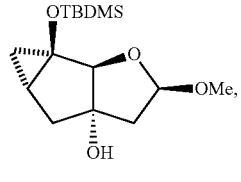
(VIII)

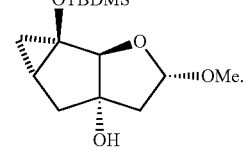
(IX)

3. The method of claim 1, wherein the solvent comprises hexanes, toluene, dichloromethane ($CH_2Cl_2$), tetrahydrofuran (THF), acetonitrile ($CH_3CN$), dimethylformamide (DMF), diethylether, dimethoxyethane (DME), or a combination thereof.

4. The method of claim 1, wherein the step of preparing the carbene precursor includes the step of adding a carbene additive to the mixture of Lewis acid catalyst and $R^7I_2$, wherein the carbene additive is selected from the group consisting of substituted or unsubstituted alkyl alcohol, carboxylic acid, and phosphate.

5. The method of claim 1, wherein the carbene precursor is $Q_3CCO_2ZnR^7I$, $Q_3CCH_2OZnR^7I$, $(n\text{-}BuO)_2P(O)OZnR^7I$, $(alkyl\text{-}O)_2P(O)OZnR^7I$, $(aryl\text{-}O)_2P(O)OZnR^7I$, or $2,4,6\text{-}Cl_3C_6H_2OZnR^7I$, wherein each Q is independently selected from the group consisting of H, Cl, Br, and F, and $R^7$ is selected from the group consisting of $CH_2$, $CH-C_{1-6}$alkyl, $CH-C_{2-6}$alkenyl, $CH-C_{2-6}$alkynyl, substituted $CH-C_{1-6}$alkyl, substituted $CH-C_2\text{-}6$alkenyl, substituted $CH-C_{2-6}$alkynyl, and $CH-(CH_2)_n-C(O)-R^8$, wherein n is 0 to 6 and wherein $R^8$ is selected from the group consisting of OH, $NH_2$, $O\text{-}C_{1-32}$alkyl and $NH-C_{1-32}$alkyl.

6. The method of claim 1, wherein the carbene precursor is $CCl_3CO_2ZnCH_2I$, $CF_3CH_2OZnCH_2I$, $(n\text{-}BuO)_2P(O)OZnCH_2I$, or $2,4,6\text{-}Cl_3C_6H_2OZnCH_2I$.

7. The method of claim 1, wherein the first Lewis acid and the second Lewis acid are each independently selected from the group consisting of $Et_2AlCl$, $Et_2Zn$, $ZnI_2$, $ZnCl_2$, $ZnBr_2$, $Ti(OiPr)_4$, $Me_2AlCl$, TMSOTf, $TiCl_4$, and combinations thereof.

8. The method of claim 1, wherein the first Lewis acid is $Et_2Zn$.

9. The method of claim 2, wherein the solvent comprises hexanes, toluene, dichloromethane ($CH_2Cl_2$), tetrahydrofuran (THF), acetonitrile ($CH_3CN$), dimethylformamide (DMF), diethylether, dimethoxyethane (DME), or a combination thereof.

10. The method of claim 2, wherein the step of preparing the carbene precursor includes the step of adding a carbene additive to the mixture of Lewis acid catalyst and $R^7I_2$, wherein the carbene additive is selected from the group consisting of substituted or unsubstituted alkyl alcohol, carboxylic acid, and phosphate.

11. The method of claim 2, wherein the carbene precursor is $Q_3CCO_2ZnR^7I$, $Q_3CCH_2OZnR^7I$, $(n\text{-}BuO)_2P(O)OZnR^7I$, $(alkyl\text{-}O)_2P(O)$ $OZnR^7I$, $(aryl\text{-}O)_2P(O)OZnR^7I$, or $2,4,6\text{-}Cl_3C_6H_2OZnR^7I$, wherein each Q is independently selected from the group consisting of H, Cl, Br, and F, and $R^7$ is selected from the group consisting of $CH_2$, $CH-C_{1-6}$alkyl, $CH-C_2\text{-}6$alkenyl, $CH-C_{2-6}$alkynyl, substituted $CH-C_{1-6}$alkyl, substituted $CH-C_{2-6}$alkenyl, substituted $CH-C_{2-6}$alkynyl, and $CH\text{-}(CH_2)\,n\text{-}C(O)-R^8$, wherein n is 0 to 6 and wherein $R^8$ is selected from the group consisting of OH, $NH_2$, $O-C_{1-32}$alkyl and $NH-C_{1-32}$alkyl.

12. The method of claim 2, wherein the carbene precursor is $CCl_3CO_2ZnCH_2I$, $CF_3CH_2OZnCH_2I$, $(n\text{-}BuO)_2P(O)OZnCH_2I$, or $2,4,6\text{-}Cl_3C_6H_2OZnCH_2I$.

13. The method of claim 2, wherein the first Lewis acid and the second Lewis acid are each independently selected from the group consisting of $Et_2AlCl$, $Et_2Zn$, $ZnI_2$, $ZnCl_2$, $ZnBr_2$, $Ti(OiPr)_4$, $Me_2AlCl$, TMSOTf, $TiCl_4$, and combinations thereof.

14. The method of claim 2, wherein the first Lewis acid is $Et_2Zn$.

* * * * *